United States Patent
Hsu

(10) Patent No.: US 6,449,503 B1
(45) Date of Patent: Sep. 10, 2002

(54) CLASSIFICATION OF SUPRAVENTRICULAR AND VENTRICULAR CARDIAC RHYTHMS USING CROSS CHANNEL TIMING ALGORITHM

(75) Inventor: William Hsu, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/352,056

(22) Filed: Jul. 14, 1999

(51) Int. Cl.⁷ ............................................. A61B 5/0464
(52) U.S. Cl. ......................................... 600/518; 607/14
(58) Field of Search ................................ 600/517, 510, 600/516, 515, 518; 607/4, 5, 14

(56) References Cited

U.S. PATENT DOCUMENTS

| | | |
|---|---|---|
| 4,336,810 A | 6/1982 | Anderson et al. |
| 4,838,278 A | 6/1989 | Wang et al. |
| 5,215,098 A | 6/1993 | Steinhaus et al. |
| 5,240,009 A | 8/1993 | Williams |
| 5,255,186 A | 10/1993 | Steinhaus et al. |
| 5,311,874 A | 5/1994 | Baumann et al. |
| 5,331,966 A | 7/1994 | Bennett et al. |
| 5,400,795 A | 3/1995 | Murphy et al. |
| 5,447,519 A * | 9/1995 | Peterson .................... 607/5 |
| 5,503,159 A | 4/1996 | Burton ..................... 128/703 |
| 5,609,158 A | 3/1997 | Chan ....................... 128/705 |
| 5,628,326 A | 5/1997 | Arand et al. |
| 5,704,365 A | 1/1998 | Albrecht et al. |
| 5,779,645 A | 7/1998 | Olson et al. |
| 5,868,680 A | 2/1999 | Steiner et al. .............. 600/518 |
| 5,935,082 A | 8/1999 | Albrecht et al. |
| 5,954,661 A | 9/1999 | Greenspon et al. |

FOREIGN PATENT DOCUMENTS

| | | | |
|---|---|---|---|
| EP | 0506230 | 9/1992 | ........ A61B/5/0464 |
| EP | 0 506 230 | 9/1992 | |
| EP | 0776630 | 6/1997 | ........ A61B/5/0452 |
| WO | WO 97/39681 | 10/1997 | |

* cited by examiner

Primary Examiner—George R. Evanisko
(74) Attorney, Agent, or Firm—Schwegman, Lundberg, Woessner & Kluth, P.A.

(57) ABSTRACT

A system and method for classifying cardiac complexes sensed during a tachycardia episode. A first cardiac signal and a second cardiac signal are sensed, where the first cardiac signal has a voltage. A first cardiac complex and a second cardiac complex of a cardiac cycle are detected in the first and second cardiac signal, respectively. A predetermined alignment feature is identified in the second cardiac complex. A datum is defined, or positioned, at a specified interval from the predetermined alignment feature of the second cardiac complex. Voltage values are then measured from the first cardiac complex at each of two or more measurement intervals from the datum. The voltage values are then compared voltage values measured from NSR cardiac complexes to classify the first cardiac complex is either a ventricular tachycardia complex or a supraventricular tachycardiac complex.

16 Claims, 18 Drawing Sheets

CLASSIFICATION OF SUPRAVENTRICULAR AND VENTRICULAR CARDIAC RHYTHMS USING CROSS CHANNEL TIMING ALGORITHM

FIELD OF THE INVENTION

The subject matter relates generally to medical devices and more particularly to classification of sensed cardiac complexes.

BACKGROUND

Effective, efficient ventricular pumping action depends on proper cardiac function. Proper cardiac function, in turn, relies on the synchronized contractions of the heart at regular intervals. When normal cardiac rhythm is initiated at the sinoatrial node, the heart is said to be in sinus rhythm. However, when the heart experiences irregularities in its coordinated contraction, due to electrophysiologic disturbances caused by a disease process or from an electrical disturbance, the heart is denoted to be arrhythmic. The resulting cardiac arrhythmia impairs cardiac efficiency and can be a potential life threatening event.

Cardiac arrhythmias occurring in the atrial region of the heart are called supraventricular tachyarrhythmias (SVTs). Cardiac arrhythmias occurring in the ventricular region of the heart are called ventricular tachyarrhythmias (VTs). SVTs and VTs are morphologically and physiologically distinct events. VTs take many forms, including ventricular fibrillation and ventricular tachycardia. Ventricular fibrillation is a condition denoted by extremely rapid, nonsynchronous contractions of the ventricles. This condition is fatal unless the heart is returned to sinus rhythm within a few minutes. Ventricular tachycardia are conditions denoted by a rapid heart beat, 150 to 250 beats per minute, that has its origin in some abnormal location within the ventricular myocardium. The abnormal location is typically results from damage to the ventricular myocardium from a myocardial infarction. Ventricular tachycardia can quickly degenerate into ventricular fibrillation.

SVTs also take many forms, including atrial fibrillation and atrial flutter. Both conditions are characterized by rapid uncoordinated contractions of the atria. Besides being hemodynamically inefficient, the rapid contractions of the atria can also adversely effect the ventricular rate. This occurs when the aberrant contractile impulse in the atria are transmitted to the ventricles. It is then possible for the aberrant atrial signals to induce VTs, such as a ventricular tachycardia.

Implantable cardioverter/defibrillators (ICDs) have been established as an effective treatment for patients with serious ventricular tachyarrhythmias. The first generation of ICDs relied exclusively on ventricular rate sensing for tachyarrhythmia detection. Specificity to SVT was, however, often compromised, especially when the ventricular response to SVT surpassed the patient's heart rate during VT. The frequency of inappropriate shocks with early generations of signal chamber ICDs ranged from 10–41% of the shocks. Detection enhancements, such as Sudden Onset and Stability of the cardiac rhythms, improved specificity in more modem ICDs. The introduction of dual chamber defibrillators further improved upon the specificity to SVT without compromising sensitivity to VT. unfortunately, some patients still receive inappropriate therapies for SVT, especially when atria-to-ventricular conduction is 1:1.

Morphology-based algorithms have been proposed as a way of distinguishing VT from SVT. Many of these algorithms are template matching algorithms which determine the type of tachycardia by comparing features of the electrogram in question with an efficient representation of the patient's normal sinus rhythm (NSR) electrogram. The basis of appropriate discrimination using template-matching algorithms are based on the assumption that the morphology of ventricular depolarization during VT will be dissimilar to those during NSR. These algorithms classify cardiac complexes based on their morphological similarity to the patient's NSR complexes using only one intracardiac electrogram channel. In the process of comparing any two complexes, the algorithm locates a fuducial point (e.g., the peak of the complex) to align the two complexes with respect to each other. This alignment has the side effect of positioning complexes such that they appear to be more similar then they actually are. As a result, differentiating the two complexes becomes more difficult.

For the reasons stated above, and for other reasons stated below which will become apparent to those skilled in the art upon reading and understanding the present specification, there is a need in the art for providing a reliable system of discriminating SVT induced ventricular tachycardia from malignant ventricular tachycardia which can provide effective and reliable therapy to patients experiencing malignant ventricular tachycardia.

SUMMARY OF THE INVENTION

The present subject matter is directed to a system and a method for distinguishing between the occurrence of a ventricular tachycardia (VT) and a supraventricular tachycardia (SVT) during a tachycardia episode. Upon detecting a tachycardia episode, the system measures voltage values from predetermined positions along sensed cardiac signals. The voltage values are then compared to voltage values measured at the same relative positions along model cardiac complexes. Using this comparison, the system is able to distinguish the underlying cause of a tachycardia episode as either being an SVT or as a VT.

Initially, a first model cardiac complex and a second model cardiac complex are detected, or sensed, in the first cardiac signal and the second cardiac signal, respectively. In one embodiment, the first and second model cardiac complexes are normal sinus rhythm (NSR) cardiac complexes sensed during normal sinus rhythm. Alternatively, the first and second model cardiac complexes are cardiac complexes which are induced by electrical pulses delivered to at least one supraventricular location of the heart.

As the second model cardiac complex is sensed, a predetermined alignment feature is identified. In one embodiment, the predetermined alignment feature of the second cardiac complex is a repeatably identifiable portion of the second cardiac complex, such as a maximum deflection point of the second cardiac complex. The predetermined alignment feature is then used to define, or position, a datum at a specified interval from the predetermined alignment feature. In one embodiment, the datum can be thought of as a line, or a position, from which to make voltage measurements along the first cardiac signal during the first cardiac complex. In one embodiment, the datum is positioned at any location between two sensed cardiac complexes.

Once the datum has been positioned relative the predetermined alignment feature, a specified interval is measured between the predetermined alignment feature and the datum. Two or more morphological features are then selected along the first model cardiac complex. A measurement interval is then measured between the datum and each of the morphological features on the first model cardiac complex. In addition to measuring the measurement intervals, the voltage value of the first model cardiac complex at each of the measurement intervals is measured from the first model cardiac signal. The values and locations of the predetermined alignment feature, the specified interval and the measurement intervals are then recorded and stored for use in classifying cardiac complexes as either VT or SVT cardiac complexes during a tachycardia episode.

When a tachycardia episode is detected, a first cardiac complex and a second cardiac complex of a cardiac cycle are detected, or sensed, in the first cardiac signal and the second cardiac signal, respectively. As the second cardiac complex is sensed, the predetermined alignment feature is identified. The predetermined alignment feature is then used to define, or position, the datum at the specified interval from the predetermined alignment feature. Once the datum has been positioned relative the predetermined alignment feature, a voltage value is measured at each of the two or more measurement intervals from the datum along the first cardiac signal. The voltage values measured from the first cardiac signal are then compared voltage values measured from model complexes. Based on the comparison, the first cardiac complex is classified as either a VT complex or a SVT complex.

As the tachycardiac episode occurs, a plurality of cardiac cycles are detected in the first cardiac signal and the second cardiac signal. A predetermined number of the first cardiac complexes are classified as either VT or SVT cardiac complexes based on the present subject matter. A ventricular tachycardia episode is then declared when a threshold number of the predetermined number of the first cardiac complexes are classified as ventricular tachycardia complexes. Alternatively, a supraventricular tachycardia episode is declared when the threshold number of the predetermined number of the first cardiac complexes are classified as supraventricular tachycardia complexes.

In an additional embodiment, the present subject matter provides for a system and method of creating a template for a morphology-based algorithm which is used to classify cardiac complexes during a tachycardia episode. In one embodiment, electrical energy pulses are provided to the supraventricular region of the patient's heart. The resulting cardiac complexes are then sensed and used to create a template for use in a morphology-based cardiac classification algorithm for classifying, categorizing or assessing a patient's cardiac condition.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The present subject matter allows for a cardiac complex to be quickly and accurately classified as either being an arrhythmic cardiac complex or a non-arrhythmic cardiac complex. One application of the present subject matter is in classifying cardiac complexes sensed during a tachycardia episode as either ventricular tachycardia (VT) or supraventricular tachycardia (SVT) complexes. Based on the classification of the cardiac complexes, the tachycardia episode can then be classified as either a VT or an SVT event. In one embodiment, the present subject matter is useful in classifying a tachycardia episode having a 1:1 atrial-to-ventricular ratio.

Figure 1:
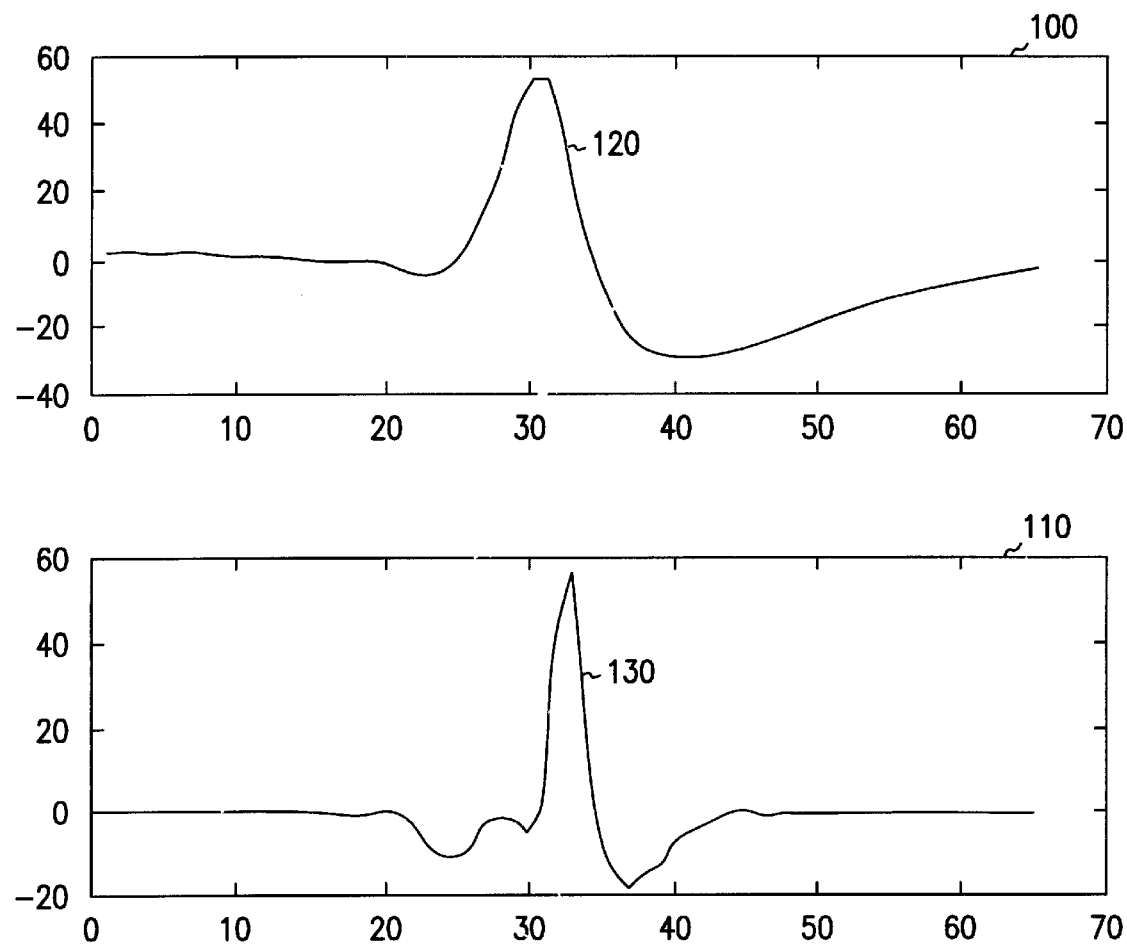
FIG. 1 shows a first cardiac signal and a second cardiac signal which include a first and a second cardiac complex, respectively.

In one embodiment the present subject matter uses cardiac signals sensed in two cardiac channels to classify cardiac complexes during a tachycardia episode. Using two cardiac channels allows for a more complete "view" of each cardiac complex from which to classify the cardiac complex. For example, two cardiac channels useful for the present subject matter include a ventricular far-field channel and a ventricular near-field channel. FIG. 1 shows one example of a cardiac complex as it was sensed in a far-field channel 100 and a near-field channel 110. The cardiac signals are plotted as a voltage of the cardiac signal (y-axis) as a function of time (x-axis). In the far-field channel 100, the cardiac complexes are sensed between defibrillation electrodes which provides a signal representative of a larger region of contracting cardiac tissue. For example, the far-field channel 100 includes a QRS-complex 120 which represents a ventricular contraction of a cardiac cycle. In the near-field channel 110, the cardiac complex are sensed between a pacing electrode and a second electrode. Due to its smaller size the pacing electrode sensing a more localized region of contracting tissue than the far-field signal. Differences in cardiac signals sensed in far-field and near-field signal are then used in the present subject matter to classify cardiac complexes during the tachycardia episode.

The relative positions of the QRS-complexes in the far-field and the near-field channels contain information about the conduction path of the cardiac action potential. SVT complexes use the same conduction path that cardiac complexes which initiate in the supraventricular region use, as the conduction problem in an SVT is present in the supraventricular region. In contrast, VT complexes do not use the same conduction path as cardiac complexes which initiate in the supraventricular region, as the conduction problem is present in the ventricular region. Besides SVT complexes originating in the SVT region, other cardiac complexes also arise in the supraventricular region. Examples include normal sinus rhythm (NSR) complexes and cardiac complexes which are initiated by pacing pulses to the supraventricular region. The similarity in cardiac complex origin between SVT cardiac complexes and NSR cardiac complexes or paced cardiac complexes, and the dissimilarity between VT cardiac complexes and the NSR cardiac complexes or paced cardiac complexes, is used in the present subject matter to help classify a cardiac complex sensed during a tachycardiac episode as either a SVT complex or a VT complex.

Figure 2:
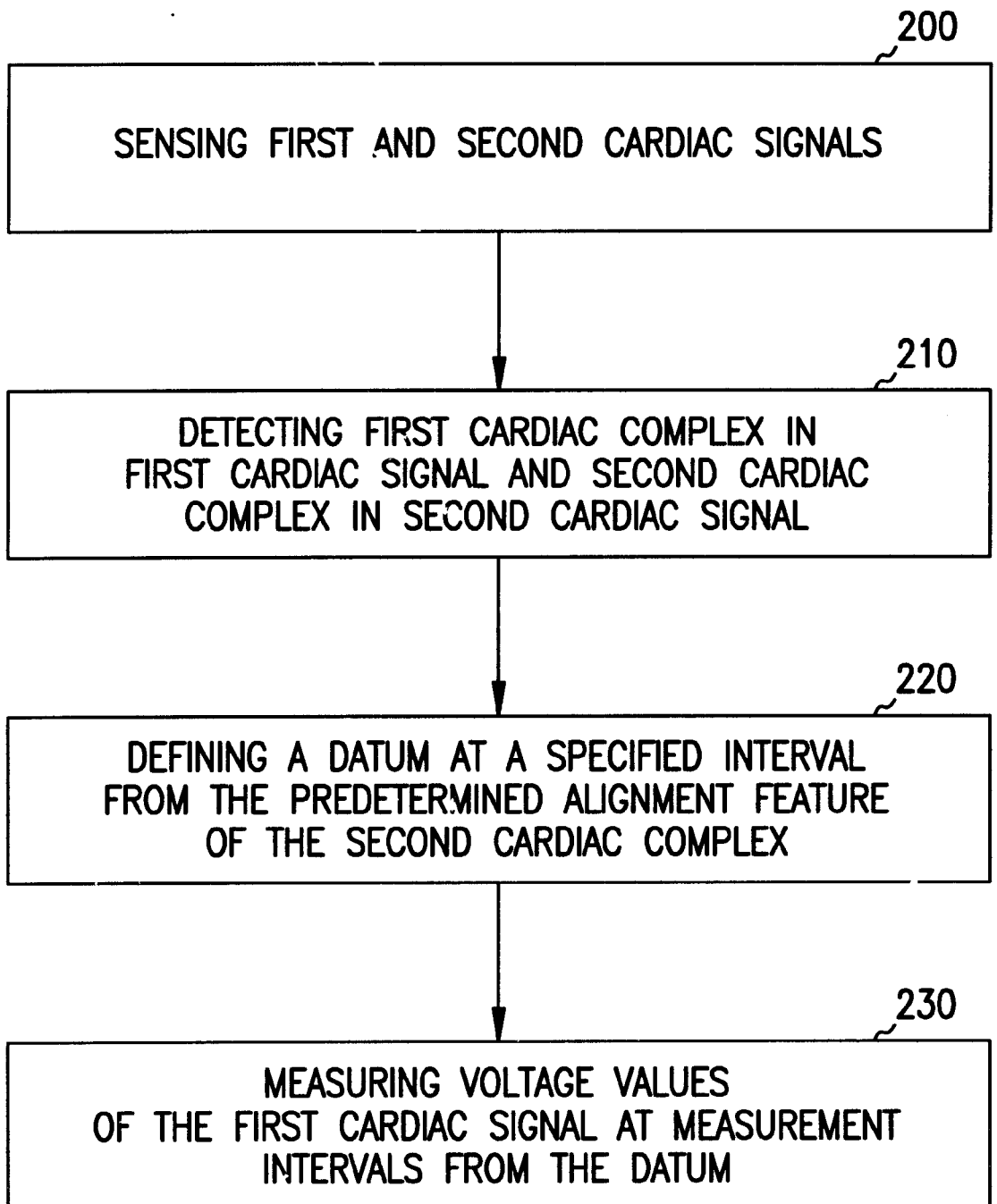
FIG. 2 is a flow diagram of one embodiment of the present subject matter.

Referring now to FIG. 2, there is shown one embodiment of the present subject matter for classifying cardiac complexes sensed during a tachyarrhythmia episode. At 200, a first cardiac signal and a second cardiac signal are sensed. Both the first and second cardiac signals include cardiac complexes which represent the cardiac cycle of the heart. As a cardiac cycle occurs, a first cardiac complex for a cardiac cycle is detected in the first cardiac signal and a second cardiac complex for the cardiac cycle is detected in the second cardiac signal at 210. At 220, a datum is positioned relative the first and second cardiac complexes. In one embodiment, the datum is a reference point or line from which distances (or times) are measured prior to taking voltage measurements from the first and second cardiac signals.

In one embodiment, the datum is defined, or located, at a specified interval (e.g., an interval of time) from a predetermined alignment feature located on the second cardiac complex. In one embodiment, the predetermined alignment feature is a repeatably identifiable portion of a sensed cardiac complex detected in the second cardiac signal which can be used as a reference point to align and/or coordinate the position of the first and second cardiac complexes relative the datum. In one embodiment, the predetermined alignment feature is the maximum deflection point of the second cardiac signal during a cardiac complex. In an additional embodiment, the predetermined alignment feature is a point of maximum slew. Alternatively, the predetermined alignment feature is fiducial point of the second cardiac complex. The predetermined alignment feature, however, can be any repeatably identifiable portion of the second cardiac complex which will be present regardless of the arrhythmia that is occurring.

At 230, once the datum has been defined (or positioned) relative the predetermined alignment feature, a voltage value of the first cardiac signal is measured at each of two or more measurement intervals from the datum. As will be explained full below, the voltage values measured from the first cardiac signal are used to create a complex feature vector. The complex feature vector is then compared to a template feature vector, where in one embodiment the template feature vector represents a model cardiac complex (or complexes) of a patient's heart. Based on the comparison, the cardiac complex detected in the first and second cardiac signal is then classified as either a SVT cardiac complex or a VT cardiac complex.

As the cardiac complexes are sensed during the tachycardia event they are aligned with and compared to the model cardiac complex. Because comparing an entire cardiac complex to a template can be time consuming and/or computationally difficult, the present subject matter measures voltage values from the sensed cardiac complexes and creates a vector to numerically represent the complexes. In one embodiment, model cardiac complexes are derived from cardiac complexes sensed from the patient. For example, the model cardiac complex (or complexes) is derived from cardiac complexes sensed during the patient's normal sinus rhythm (NSR). In an additional example, the model cardiac complex (or complexes) is derived from sensed "induced" cardiac complexes which are the result of a cardiac cycle initiated by electrical pulses being delivered to the supraventricular region of the heart. Each of the cardiac complexes to be classified are then represented by a complex feature vector. The complex feature vector is then compared to the template feature vector and the cardiac complex is classified based on that comparison.

Figure 3:
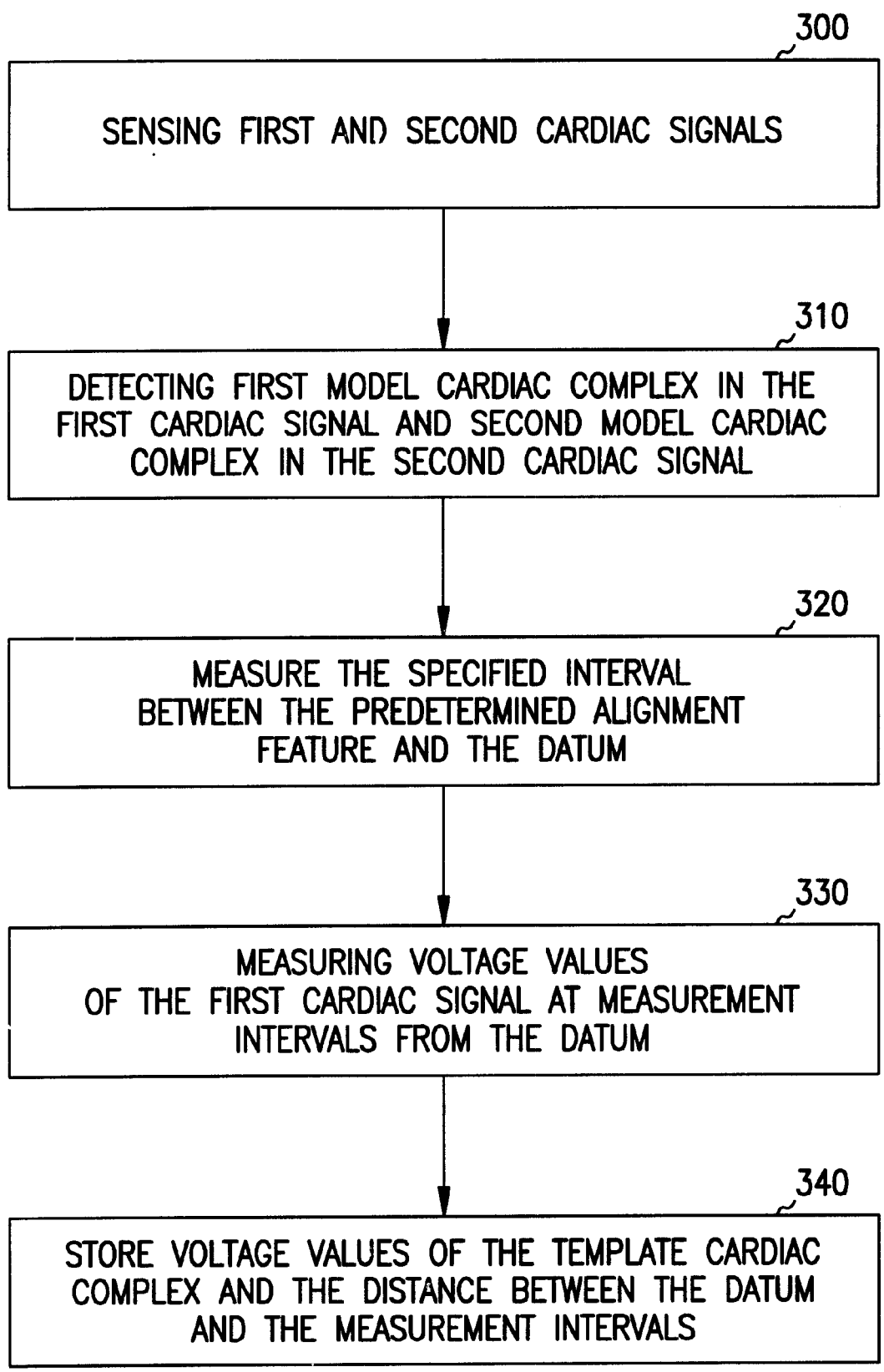
FIG. 3 is a flow diagram of one embodiment of the present subject matter.

FIG. 3 shows one embodiment of determining the specified interval and the template feature vector from the sensed model cardiac complexes. At 300, a first cardiac signal and a second cardiac signal are sensed. At 310, a first model cardiac complex is detected in the first cardiac signal, and a second model cardiac complex is detected in the second cardiac signal. In one embodiment, the first and second model cardiac complexes are representative of a cardiac cycle. A predetermined alignment feature is then located relative the second model cardiac complex at 320. In one embodiment, the predetermined alignment feature is positioned, or located, by an attending medical personal who is viewing an image of the second cardiac signal and the second model cardiac complex. In one embodiment, the image is viewed on a medical device programmer which is in communication with an implantable medical device, such as an implantable cardiac defibrillator, which is sensing the first and second cardiac signals. The predetermined alignment feature is then identified and the medical device programmer is used to program the implantable medical device as to the location of the predetermined alignment feature.

Once the predetermined alignment feature is located at 330, the specified interval between the predetermined alignment feature and the datum is measured. In one embodiment, the datum is also positioned, or located, by the attending medical personal while viewing the image of the first and second cardiac signals. At 340, the specified interval is then stored. In addition to measuring the specified interval at 350, voltage values of the first cardiac signal during the first model cardiac complex are measured at each of the two or more measurement intervals from the datum.

At 360, the voltage values of the first cardiac signal at each of the two or more measurement intervals from the datum are then stored.

Figure 4:
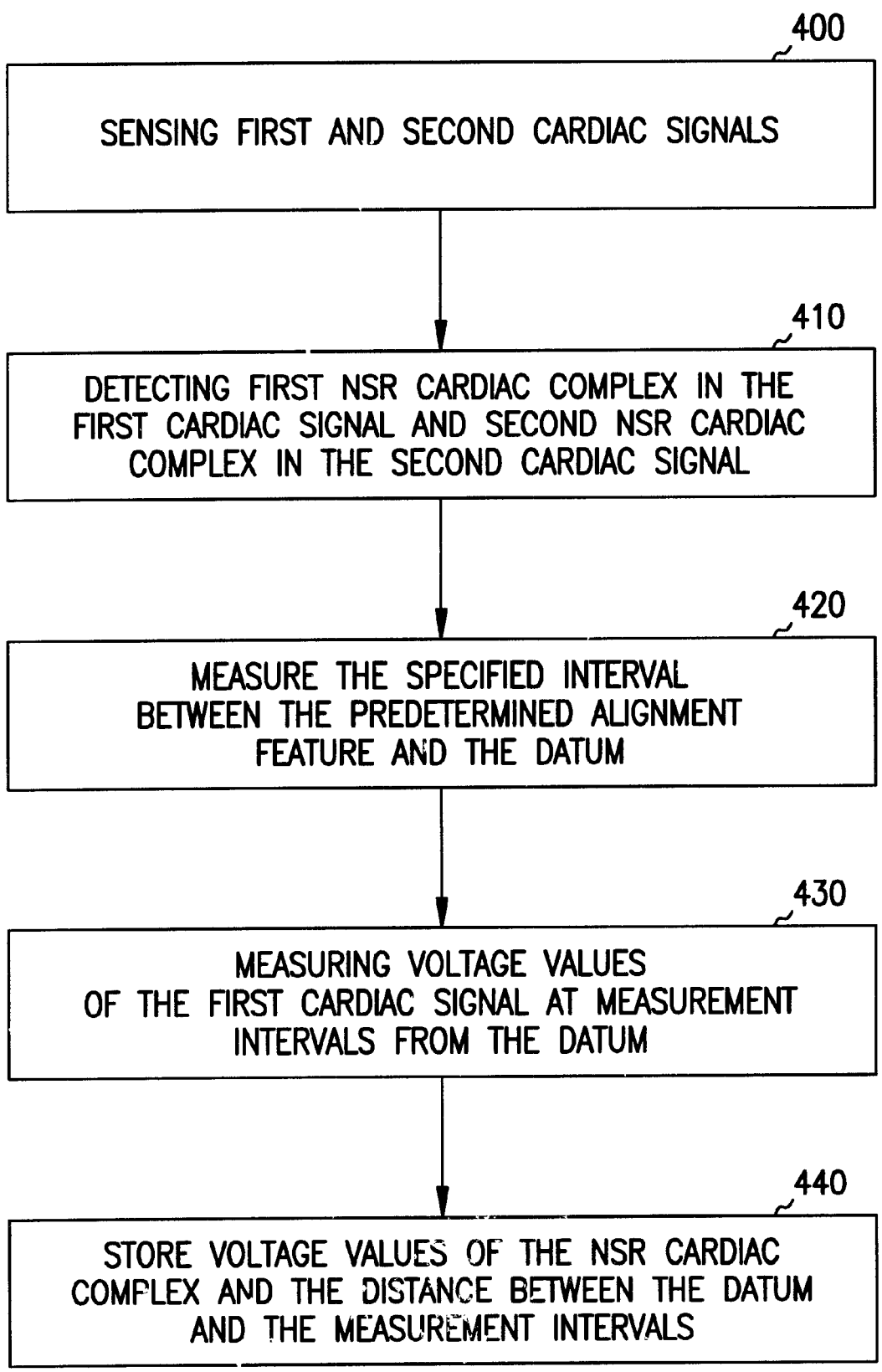
FIG. 4 is a flow diagram of one embodiment of the present subject matter.

As previously discussed, the first and second model cardiac complexes can either be sensed during the patient's normal sinus rhythm NSR) or be induced cardiac complexes sensed after electrical pulses have been delivered to the supraventricular region of the heart. FIG. 4 shows one example of determining the specified interval and the template feature vector from NSR cardiac complexes. At 400, a first cardiac signal and a second cardiac signal are sensed during the patient's NSR. At 410, first and second model cardiac complexes, in this case NSR cardiac complexes, are detected in the first and second cardiac signals, respectively. In one embodiment, the NSR cardiac complexes from which the specified interval and the template feature vector are derived can either be a signal NSR complex which is representative of a large number of NSR complexes sensed from the patient. Alternatively, an average or median NSR cardiac complex from two or more NSR cardiac complexes is used to determine the specified interval and the template feature vector. To ensure that the NSR cardiac complex used in determining an average or a median NSR cardiac complex are representative of the patient's NSR, a correlation coefficient for the NSR cardiac complex is calculated and NSR cardiac complexes having a correlation coefficient of greater then 0.90 are used to create the representative NSR cardiac complex.

In one embodiment, the patient's NSR are sensed using catheter electrodes coupled to an implantable cardioverter/defibrillator. In one embodiment, the NSR complexes are sensed on far and near field signals using intracardiac electrodes implanted within the chambers of and/or on the surface of the patient's heart. The sensed NSR cardiac complexes are then downloaded, or transferred, to a medical device programmer. In one embodiment, the medical device programmer displays NSR complexes for review and selection by attending physicians. The medical device programmer can also calculate the correlation coefficient for the NSR complexes based on morphological features of the complexes and derived a median or an average NSR complex.

Once the first and second NSR cardiac complexes have been determined, the predetermined alignment feature is identified in the second NSR cardiac complex. In one embodiment, the predetermined alignment feature is identified by the attending physician or medical personal based on the criteria previously discussed. In one embodiment, the first and second NSR cardiac complexes are displayed on the view screen of the medical device programmer. The physician or medical personnel can then identify the predetermined alignment feature on the second NSR cardiac complex. Alternatively, the predetermined alignment feature is determined using an alignment feature extraction program executed in the medical device programmer, where the attending physician or medical personal select the desired predetermined alignment feature from a predetermined list of features the medical device programmer is capable of identifying. The program then analyzes the NSR cardiac complexes to identify the predetermined alignment feature.

Once the predetermined alignment feature of the second cardiac complex is identified, the value of the specified interval is measured between the predetermined alignment feature and the datum. In one embodiment, the datum is set at a position along the first and second cardiac signals between two consecutively sensed cardiac complexes. The specified interval is then measured between the predetermined alignment feature and the datum and the value is then stored. Alternatively, the datum is set at a specified interval of time from the predetermined alignment feature, where the specified interval of time is selected so as to position the datum along the first and second cardiac signals between consecutively sensed cardiac complexes. Once the datum is set relative the predetermined alignment feature the value of the specified interval is stored for use in classifying cardiac complexes.

At 430, voltage values of the first cardiac signal are measured from the first NSR cardiac complex relative the datum. In one embodiment, the voltage values are measured at morphological features of the first NSR. The morphological features selected from the NSR cardiac complexes include maximum or minimum deflection points of the cardiac signal, the beginning or ending of the cardiac complex, fiducial points along the cardiac signals during the NSR cardiac complex. Other selected morphological features are also possible, where the features represent repeatably identifiable potion of the first cardiac complex. The distance between each of the selected morphology features and the datum is then measured and the value of each of the distances creates a measurement interval. Each of the measurement intervals is then stored for subsequent use in locating a portion of the first cardiac signal sensed during a tachycardia episode. A voltage measurement of the first cardiac signal is then made at each of the measurement interval.

In one embodiment, the voltage values measured at 430 are used to create a template feature vector (TFV). In one embodiment, the TFV=$[t_1, t_2, t_3, t_4, \ldots t_n]$, where the elements of the feature vector ($t_1-t_n$) are the voltage value measured from the first cardiac signal at each of the two or more measurement intervals from the datum. Once the TFV has been created, the TFV is stored for subsequent use in analyzing cardiac complexes during a tachycardiac event.

In one embodiment, the TFV allows the entire waveform of the first NSR cardiac complex to be represented by a series, or vector, of voltage values measured along the NSR cardiac complex. By representing the first NSR cardiac complex with the TFV, the amount of information needed to store the representation of the complex is greatly reduced compared to storing the entire signal for the NSR cardiac complex. In addition, since the NSR cardiac complex is being represented by a series of values derived from a cardiac signal the computational requirements in comparing the NSR cardiac complex to a cardiac complex sensed during a tachycardia episode are also greatly reduced as compared to having to analyze the morphology of the two cardiac complexes.

Figure 5:
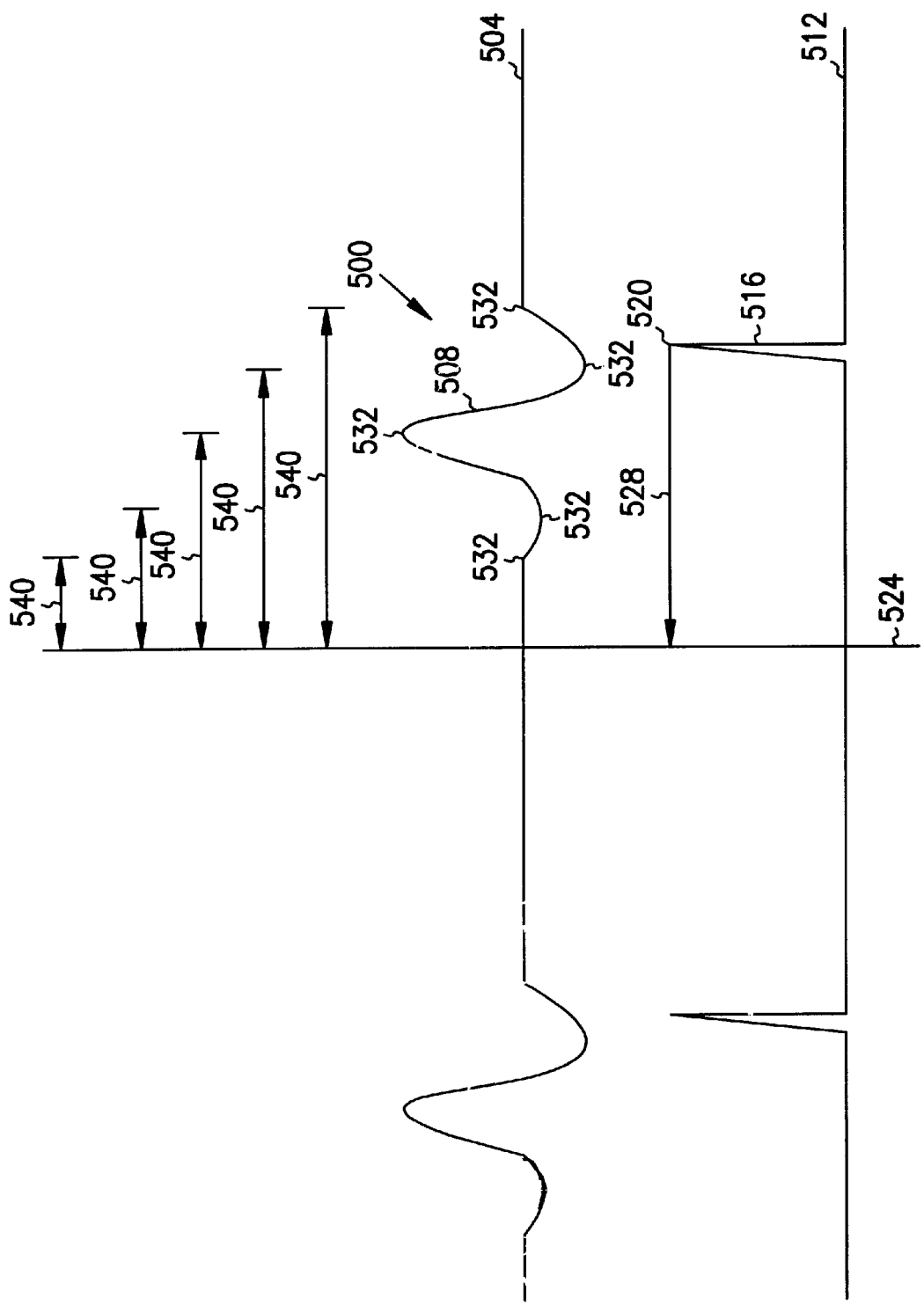
FIG. 5 shows a first cardiac signal and a second cardiac signal according to one embodiment of the present subject matter.

Referring now to FIG. 5, there is shown one embodiment of a NSR cardiac complex 500 from which a TFV and a specified interval are derived. A first cardiac signal 504 is shown having a first NSR cardiac complex 508 and a second cardiac signal 512 is shown having a second NSR cardiac complex 516. In the present embodiment, the first cardiac signal 504 is a far-field signal and the second cardiac signal 512 is a near-field signal. Other combinations of signals could be used.

A predetermined alignment feature is located along the second NSR cardiac complex 516 as previously discussed. In the present embodiment, the predetermined alignment feature is a maximum deflection point 520 of the second NSR cardiac complex 516. As previously discussed, other predetermined alignment features along the second NSR cardiac complex 516 could be selected. A datum 524 is then positioned as previously discussed at a specified interval 528 from the predetermined alignment feature.

At least two morphology features are selected on the first NSR cardiac complex 508. In the present embodiment, a plurality of morphology features are shown at 532. As previously discussed, morphology features can be selected at any number of positions along the first NSR cardiac complex 508. A measurement interval 540 is then measured between each of the selected morphology features 532 and the datum 524. The measurement intervals create the template feature vector as previously described. Additionally, each of the measurement intervals 540 is stored (e.g., the length of the measurement interval 540 are stored) so subsequent voltage measurements can be made along the first cardiac signal at, or approximately at, the same location relative the predetermined alignment feature and the datum during a tachycardiac event.

Figure 6:
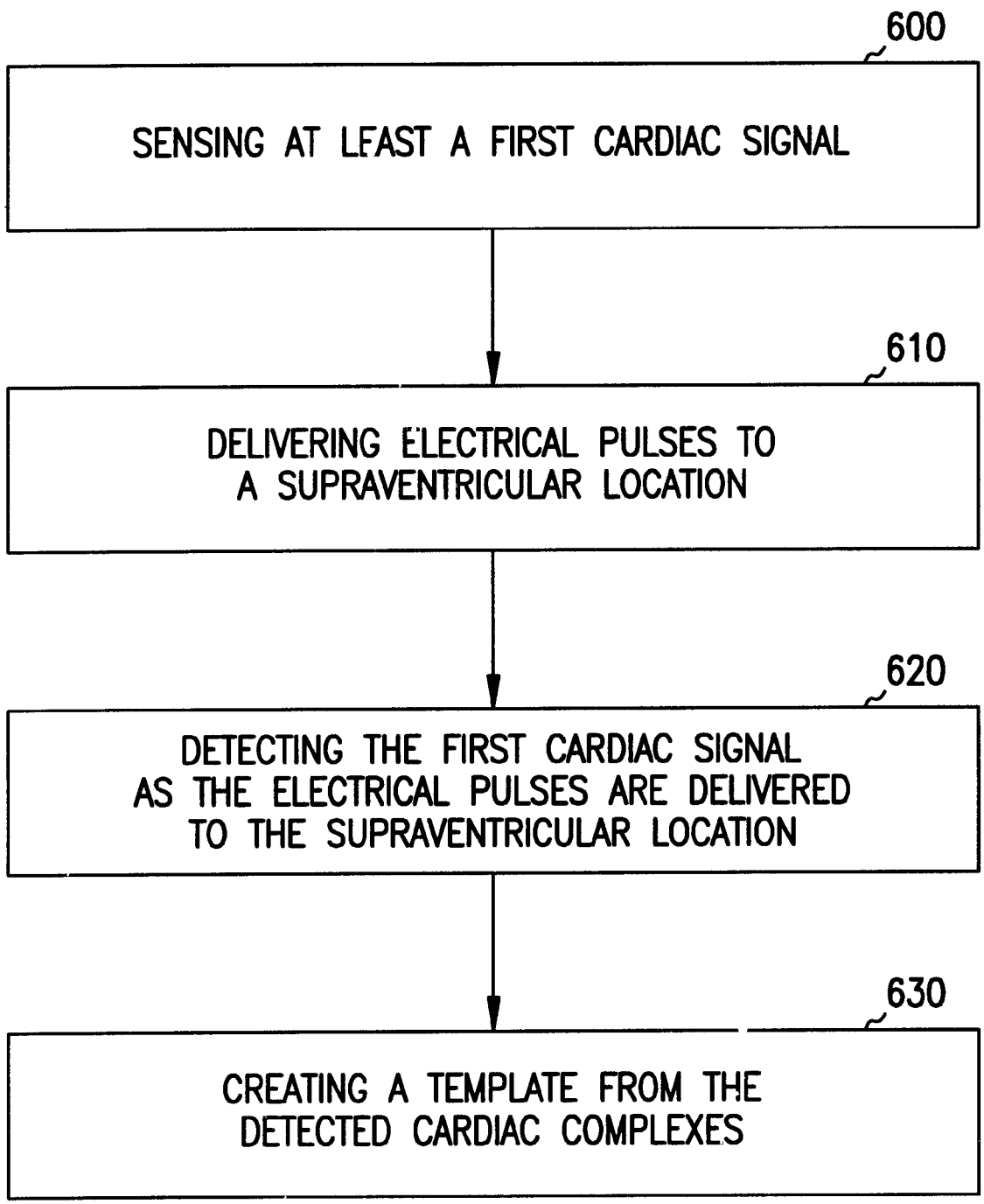
FIG. 6 is a flow diagram of one embodiment of the present subject matter.

The present subject matter recognizes that creating a template is not limited to data derived from a patient's intrinsic NSR cardiac complexes. It is also possible to provide electrical energy pulses to the supraventricular region of the patient's heart from which the resulting induced cardiac complexes are sensed and used to create a template for use in a morphology-based cardiac classification algorithm for classifying, categorizing or assessing a patient's cardiac condition. FIG. 6 shows an embodiment of creating a template for a morphology-based algorithm which is used to classify cardiac complexes during a tachyarrhythmia episode. In the present embodiment, electrical energy pulses are delivered to the supraventricular region of the heart and the resulting cardiac complexes are sensed and utilized in creating one or more templates for use in a morphology-based classification algorithm. As used herein, cardiac complexes started by the delivery of electrical energy pulses are referred to as "induced cardiac complexes."

At 600, at least a first cardiac signal is sensed from the patient's heart. By way of example only, the first cardiac signal is a far-field signal as previously discussed. At 610, electrical pulses are delivered to a supraventricular location of the patient's heart. In one embodiment, the electrical pulses are pacing level pulses delivered through a pacing electrode positioned on or within the supraventricular region of the patient's heart. The electrical pulses cause the patient's heart to proceed through a cardiac cycle which is detected as cardiac complexes in the first cardiac signal. In one embodiment, the patient is in either NSR and/or in a non-arrhythmic cardiac state. The electrical pulses are delivered to the supraventricular region, such as a right atrial location adjacent or near to the SA-node. The electrical pulses can be delivered either at the patient's intrinsic heart rate or at a rate that is above the intrinsic cardiac rate. At 620, the first cardiac signal is detected as the electrical pulses are delivered to the supraventricular location. In one embodiment, the detected first cardiac signal includes the model cardiac complexes, which in this case are the induced cardiac complexes. At 630, the detected, or sensed, induced cardiac complexes are then used to create the template or "representation" of the patient's non-arrhythmic cardiac complexes.

In one embodiment, creating the template or representation of the patient's non-arrhythmic cardiac complexes from the induced cardiac complexes is accomplished according to the present subject matter. In an alternative embodiment, creating the template or representation of the patient's non-arrhythmic cardiac complexes from the induced cardiac complexes is accomplished according to techniques and methods known for creating templates from non-induced cardiac complexes (e.g., cardiac complexes sensed during NSR). In many cases, these non-induced cardiac complexes are used to create "templates" which are subsequently used in classifying, categorizing or assessing sensed cardiac complexes during an arrhythmic episode.

Figure 7:
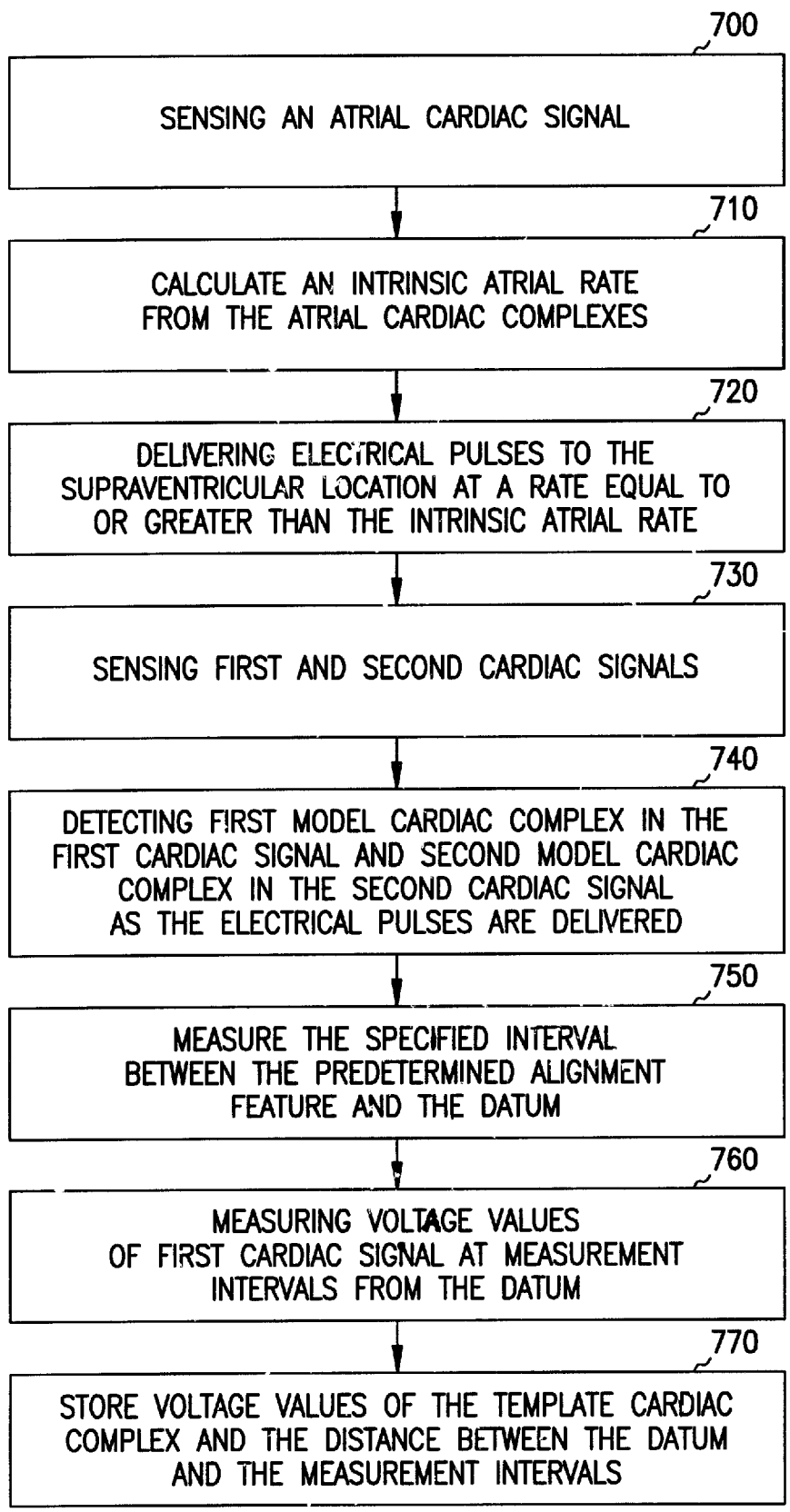
FIG. 7 is a flow diagram of one embodiment of the present subject matter.

FIG. 7 shows one embodiment of developing, or creating, a template of a classification algorithm from detected cardiac complexes from induced cardiac complexes, where the classification algorithm classifies subsequently detected cardiac complexes. At 700, an atrial cardiac signal is sensed from a supraventricular location, where the atrial cardiac signal includes atrial cardiac complexes. In one embodiment, the atrial cardiac signal is sensed with at least one implantable electrode positioned within a supraventricular location. At 710, an intrinsic atrial rate is calculated from the atrial cardiac complexes. In one embodiment, the intrinsic atrial rate is an average intrinsic atrial rate.

At 720, electrical pulses are delivered to the supraventricular location of the patient's heart at a rate that is equal to or greater than the patient's intrinsic atrial rate. In one embodiment, the electrical pulses are delivered to the supraventricular location at a predetermined rate which is faster than the average intrinsic atrial rate. In one embodiment, the predetermined rate is set at a predetermined percentage above the average intrinsic atrial rate, where the predetermined percentage is set in a range of five (5) to fifty (50), five (5) to forty (40) or ten (10) to twenty (20), where ten (10) percent is an acceptable value. In an alternative embodiment, the electrical pulses are delivered to the supraventricular location at a predetermined target heart rate. In one embodiment, the predetermined target heart rate is programmed in a range of a patient's intrinsic heart rate to one hundred sixty five (165) pulses/minute (or beats/minute), where the patient's intrinsic heart rate is in the range of forty (40) to eighty (80) beats/minute. Alternatively, the predetermined target heart rate is a programmable value in the range of forty (40) to one hundred sixty five (165), eighty (80) to one hundred sixty five (165), forty (40) to one hundred twenty (120), or eighty (80) to one hundred twenty (120) pulses/minute, where seventy (70) pulses/minute is an acceptable value.

In addition, increasing the intrinsic heart rate by delivering electrical pulses is accomplished by ramping-up, or increasing, the heart rate at a predetermined ramp acceleration. In one embodiment, the predetermined ramp acceleration is used to safely accelerate the heart rate from the intrinsic rate to the new induced heart rate (e.g., the predetermined target heart rate). In one embodiment, the predetermined ramp acceleration is programed to increase successive cardiac intervals at no more than five percent of the preceding cardiac interval. In an additional embodiment, the electrical pulses are pacing level pulses that are delivered through a pacing electrode positioned on or within the supraventricular region of the patient's heart. In one embodiment, the electrical pacing pulses are programmable voltage values in the range of 0.1 to 10, 0.1 to 5, 1 to 10, or 1 to 5 volts, where 1 volt is an acceptable value.

At 730, the first cardiac signal and the second cardiac signal are sensed from the patient's heart. At 740, first and second model cardiac complexes are detected in the first and second cardiac signals as the electrical pulses are delivered. In one embodiment, the cardiac complexes from which the specified interval and the template feature vector are derived can either be a signal cardiac complex which is representative of a large number of the induced cardiac complexes. Alternatively, an average or median cardiac complex from two or more of the induced cardiac complexes is used to determine the specified interval and the template feature vector. To ensure that the cardiac complex used in determining an average or a median cardiac complex are representative of the patient's induced cardiac complexes, a correlation coefficient for the cardiac complex is calculated and cardiac complexes having a correlation coefficient of greater then 0.90 are used to create the representative induced cardiac complex.

In one embodiment, the induced cardiac complexes are sensed using catheter electrodes coupled to an implantable cardioverter/defibrillator. In one embodiment, the induced cardiac complexes are sensed on far-field and near-field signals using intracardiac electrodes implanted within the chambers of and/or on the surface of the patient's heart. The sensed induced cardiac complexes are then downloaded, or transferred, to a medical device programmer. In one embodiment, the medical device programmer displays induced cardiac complexes for review and selection by an attending physician. The medical device programmer can also calculate the correlation coefficient for the induced cardiac complexes based on morphological features of the complexes and derived a median or an average induced cardiac complexes.

Once the first and second induced cardiac complexes have been determined, the predetermined alignment feature is identified in the second induced cardiac complex. In one embodiment, the predetermined alignment feature is identified by the attending physician or medical personal based on the criteria previously discussed. In one embodiment, the first and second induced cardiac complexes are displayed on the view screen of the medical device programmer. The physician or medical personnel can then identify the predetermined alignment feature on the second induced cardiac complex. Alternatively, the predetermined alignment feature is determined using an alignment feature extraction program executed in the medical device programmer, where the attending physician or medical personal select the desired predetermined alignment feature from a predetermined list of features the medical device programmer is capable of identifying. The program then analyzes the induced cardiac complexes to identify the predetermined alignment feature.

At 750, once the predetermined alignment feature of the second induced cardiac complex is identified the value of the specified interval is measured between the predetermined alignment feature and the datum. In one embodiment, the datum is set at a position along the first and second cardiac signals between two consecutively sensed cardiac complexes. The specified interval is then measured between the predetermined alignment feature and the datum and the value stored. Alternatively, the datum is set at a specified interval of time from the predetermined alignment feature, where the specified interval of time is selected so as to position the datum along the first and second cardiac signals between consecutively sensed cardiac complexes. Once the datum is set relative the predetermined alignment feature the value of the specified interval is stored for use in classifying cardiac complexes.

At 760, voltage values of the first cardiac signal are measured from the first induced cardiac complex relative the datum. In one embodiment, the voltage values are measured at morphological features of the first induced cardiac complex. The morphological features selected from the induced cardiac complexes include maximum or minimum deflection points of the cardiac signal, the beginning or ending of the cardiac complex, fiducial points along the cardiac signals during the induced cardiac complex. Other selected morphological features are also possible, where the features represent repeatably identifiable potion of the first induced cardiac complex. The distance between each of the selected morphology features and the datum is then measured and the value of each of the distances creates a measurement interval. At 770, each of the measurement intervals is then stored for subsequent use in locating a portion of the first cardiac signal sensed during a tachycardia episode. A voltage measurement of the first cardiac signal is then made of each of the measurement interval.

In one embodiment, the voltage values measured at 760 are used to create the template feature vector (TFV). In one embodiment, the TFV=$[t_1, t_2, t_3, t_4, \ldots, t_n]$, where the elements of the feature vector $(t_1-t_n)$ are the voltage value measured from the first induced cardiac signal at each of the two or more measurement intervals from the datum. Once the TFV has been created, the TFV is stored for subsequent use in analyzing cardiac complexes during a tachycardiac event.

In one embodiment, the TFV allows the entire waveform of the first induced cardiac complex to be represented by a series, or vector, of voltage values measured along the induced cardiac complex. By representing the first induced cardiac complex with the TFV, the amount of information needed to store the representation of the complex is greatly reduced compared to storing the entire signal for the induced cardiac complex. In addition, since the induced cardiac complex is being represented by a series of values derived from a cardiac signal the computational requirements in comparing the induced cardiac complex (i.e., the model cardiac complex) to a cardiac complex sensed during a tachycardia episode are also greatly reduced as compared to having to analyze the morphology of the two cardiac complexes.

Figure 8:
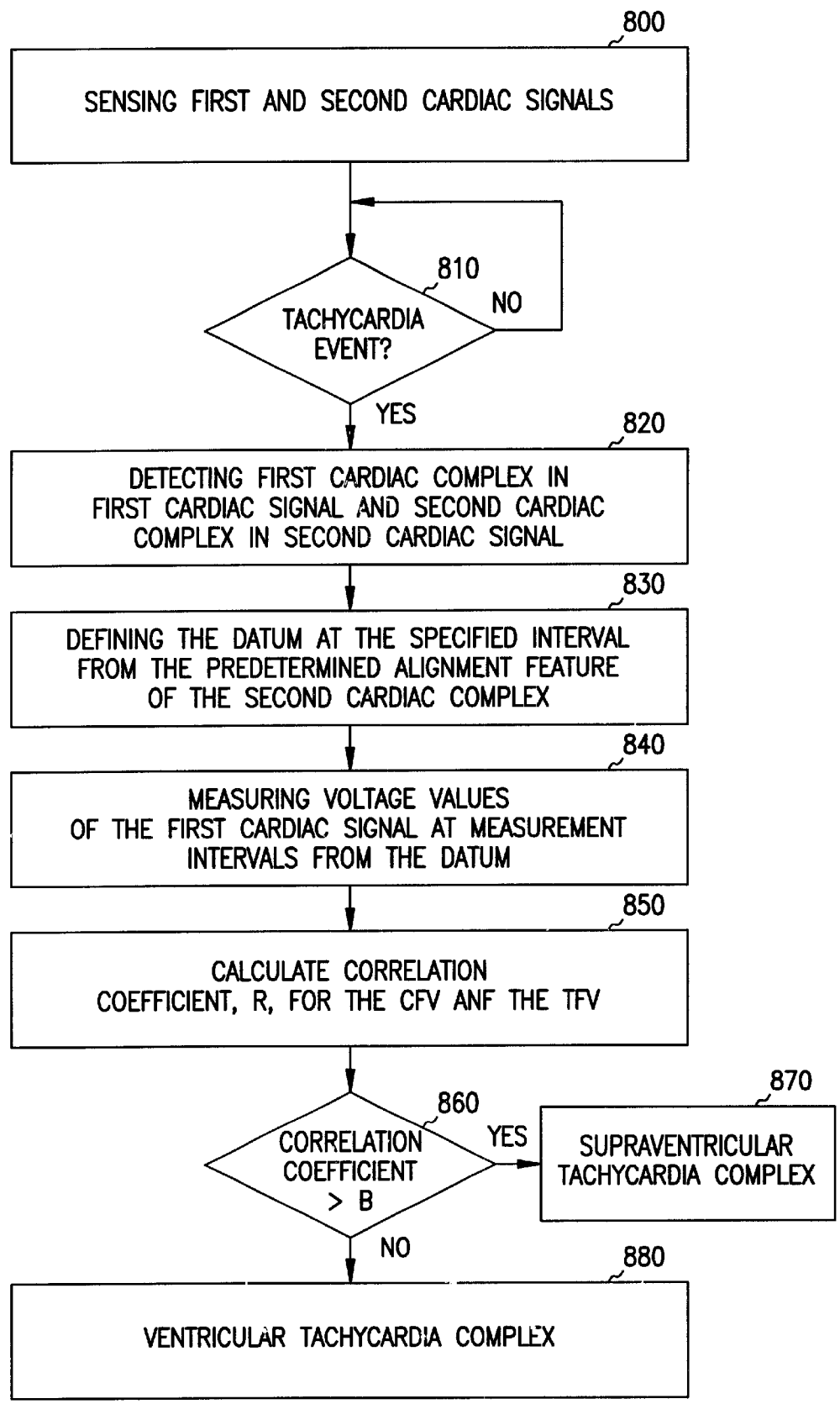
FIG. 8 is a flow diagram of one embodiment of the present subject matter.

Referring now to FIG. 8, there is shown one embodiment of classifying a cardiac complex sensed during a tachycardia episode. At 800, a first cardiac signal and a second cardiac signal are sensed. At 810, the first and second cardiac signals are analyzed to determine whether a tachycardia episode is occurring. In one embodiment, a tachycardia episode is detected when a sensed ventricular rate exceeds a predetermined threshold. In one embodiment, the predetermined threshold is set between 150 to 180 beats per minute. When the ventricular rate does not exceed the predetermined threshold, path 814 is taken back to 810 and the ventricular rate is analyzed again to determine if a tachycardiac event is occurring. Alternatively, when the ventricular rate exceeds the predetermined threshold, path 818 is taken to 820.

At 820, a first cardiac complex and a second cardiac complex are of a sensed cardiac cycle detected in the first and second cardiac signals, respectively. As each cardiac complex is sensed, voltage measurements are made from the cardiac signals. The voltage measurements are then used to create a complex feature vector (CFV) for each sensed cardiac complex. The CFV is then compared to the TFV to classify each of the sensed cardiac complexes as either SVT complexes or VT complexes.

At 830, the second cardiac complex is analyzed to locate the predetermined alignment feature. As previously discussed, the predetermined alignment feature of the second cardiac complex is the same feature located in the second model cardiac complex. In addition to locating the predetermined alignment feature, the datum is defined at the specified interval from the predetermined alignment feature on the second cardiac complex.

Figure 9:
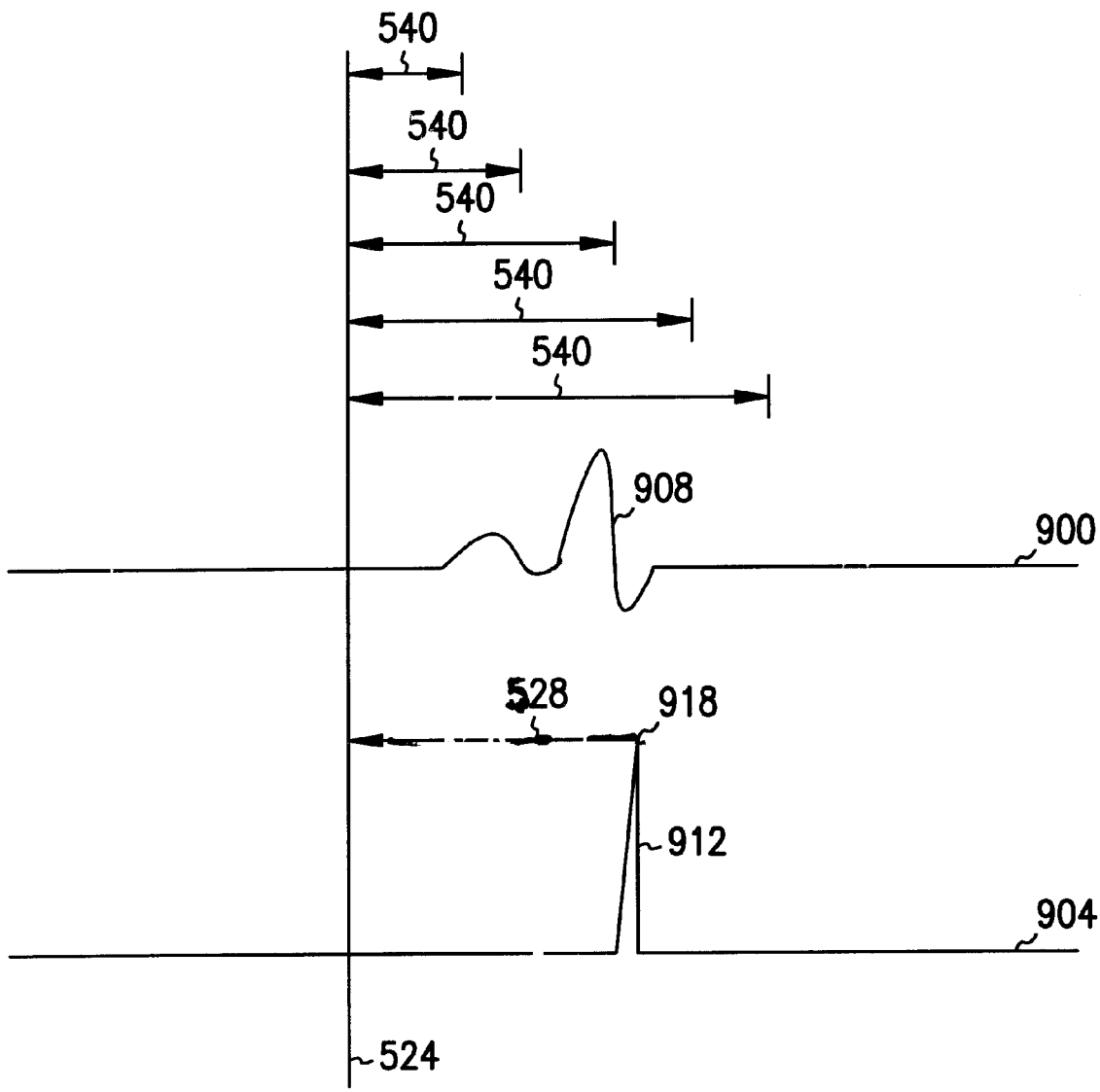
FIG. 9 shows a first cardiac signal and a second cardiac signal according to one embodiment of the present subject matter.

FIG. 9 shows an example of a cardiac complex sensed during a tachycardia episode. The first cardiac signal and the second cardiac are shown at 900 and 904, respectively. The first and second cardiac signals show a first cardiac complex 908 and a second cardiac complex 912 which represent a portion of a cardiac cycle sensed during a tachycardia episode. In the present embodiment, the predetermined alignment feature is a maximum deflection point 918 in the second cardiac complex, which was the predetermined alignment feature used in establishing the specified interval and the TFV from the NSR cardiac complex. The specified interval 528 is then used to define the position of the datum 524.

In an additional embodiment, the datum is defined at a scaling percentage of the specified interval from the predetermined alignment feature. A reason for scaling the specified interval is that during a tachycardia episode the cardiac complexes occur more rapidly. As a result the time between subsequent cardiac complexes is shorter than during either NSR or the rate of the induced cardiac complexes. Thus, the specified interval may need to be reduced by the scaling percentage, where the specified interval is multiplied by the scaling percentage to give a revised specified interval. In addition to scaling the specified interval, the measurement intervals are also scaled in the same manner as the specified interval. In one embodiment, each of the two or more measurement intervals is multiplied by the scaling percentage to give revised measurement intervals. The voltage value of the first cardiac signal for the first cardiac complex are then measured at each of two or more revised measurement intervals from the datum. In one embodiment, the scaling percentage is a function of the sensed ventricular rate, where the scaling percentage decreases as the ventricular rate increases, where the scaling percentage is programmed at a value between 50 and 100 percent.

Referring again to FIG. 8, at 840 voltage values of the first cardiac signal are measured at the measurement intervals relative the datum. As previously discussed, the measurement intervals for each of the elements of the TFV were recorded and stored for use in analyzing a tachycardiac complex during a tachycardia episode. Unlike having to identify morphological features to create the measurement intervals in the first model complex measuring the voltage values from the first cardiac complex does not rely on identifying the same morphological features used to create the measurement intervals. In analyzing and classifying the cardiac complex, the measurement intervals are used to measure the distance, or the interval, from the datum to the points, or areas, at which voltage measurements are made from the first cardiac signal. Therefore, one advantage of the present subject matter is that morphological features on the first cardiac complex sensed during a tachycardia episode do not need to be identified prior to making voltage measurements from the first cardiac signal.

Referring again to FIG. 9, there is shown one embodiment of measuring voltage values from the first cardiac signal 900 at the measurement intervals. By way of example, the measurement intervals are taken as the measurement intervals 540 defined in FIG. 5. In FIG. 5, five voltage measurements were made at five different measurement intervals 540 which gave a five element TFV=$[t_1, t_2, t_3, t_4, t_5]$. The same measurement intervals 540 are used to measure the distance from the datum 524 at which the voltage measurements are to be made along the first cardiac signal 900. The voltage values are then used to create the cardiac feature vector (CFV), CFV=$[c_1, c_2, c_3, c_4, \ldots, c_n]$, where the elements of the cardiac feature vector ($c_1$–$c_n$) are the voltage value measured from the first cardiac signal at each of the two or more measurement intervals from the datum. In the present embodiment because the same number of measurement intervals are used to measure voltage values from the first cardiac signal as were measured from the first model cardiac complex (e.g., NSR cardiac complex or induced cardiac complex), a five element CFV is created CFV=$[c_1, c_2, c_3, c_4, c_5]$.

Referring again to FIG. 8, once the voltage values of the first cardiac signal have been measured at the measurement intervals from the datum, the voltage values of the first cardiac complex and the model cardiac complex are compared to determine whether the cardiac complex is an SVT cardiac complex or a VT cardiac complex. At 850, the comparison between the two cardiac complexes is accomplished using the CFV of the cardiac complex and the TFV of the model cardiac complex. One example of comparing the CFV and the TFV is to calculate a correlation coefficient, r, of the CFV and the TFV as follows:

$$r = \text{correcoef}(TFV, CFV)$$

where correcoef (TFV, CFV) is the correlation coefficient between vectors TFV and CFV. A value of +1.0 means that TFV and CFV are correlated. As the correlation coefficient, r, value falls below 1.0 the cardiac complex becomes less correlated with the model cardiac complex.

At 860, the correlation coefficient computed for the TFV and the CFV for the cardiac complex is then compared to a predetermined threshold, $\beta$. When the correlation coefficient is greater than the predetermined threshold, the cardiac complex is classified as a SVT cardiac complex at 870. When the correlation coefficient is less than or equal to the predetermined threshold, the cardiac complex is classified as a VT cardiac complex at 880.

In one embodiment, once a tachycardiac episode is detected, a plurality of cardiac cycles are sensed and classified according to the present subject matter. The classified cardiac complexes are then used to classify the tachycardia episode as either a ventricular tachycardia episode or a supraventricular tachycardia episode. An example of classifying the tachycardia episode include using an X out of Y criterion, where Y is a predetermined number of cardiac complexes (e.g., first cardiac complexes) which are sensed and classified. In one embodiment, Y defines a window of consecutively sensed cardiac complexes, where the window has a predetermined number of sensed cardiac complexes and a new window occurs with each consecutive cardiac complex. When a threshold number of the first cardiac complexes are classified as either VT or SVT complexes during a window of Y cardiac complexes the tachycardia episode is classified (or declared) as either being a ventricular tachycardia episode or a supraventricular tachycardia episode. In one embodiment, Y is a programmable value in the range of 8 to 50, where 10 is an acceptable number of cardiac complexes. X is also a programmable value in the range of 5 to 10, where 7 is an acceptable number when the number 10 is programmed for X.

In an alternative embodiment, a percentage threshold of the classified cardiac complexes is used to classify the tachycardia episode. For example, after classifying the cardiac complex a percentage of the classified cardiac complexes is calculated for the plurality of sensed cardiac cycles. The calculated percentage of VT complexes and SVT complexes sensed during the tachycardia episode is compared to the percentage threshold. So, a ventricular tachycardia episode is declared when the threshold percentage of the first cardiac complexes from the plurality of cardiac cycles are classified as ventricular tachycardia complexes. Alternatively, a supraventricular tachycardia episode is declared when the threshold percentage of the first cardiac complexes from the plurality of cardiac cycles are classified as supraventricular tachycardia complexes. In one embodiment, the predetermined percentage threshold is a programmable value in the range of 50 to 100 percent, where a value of approximately 70 percent is an acceptable value. The plurality of cardiac complexes used in calculating the percentage of VT and SVT complexes is also a programmable number, where the plurality of cardiac complexes is programmed in the range of between 8 to 50, where 10 is an acceptable value.

Figure 10:
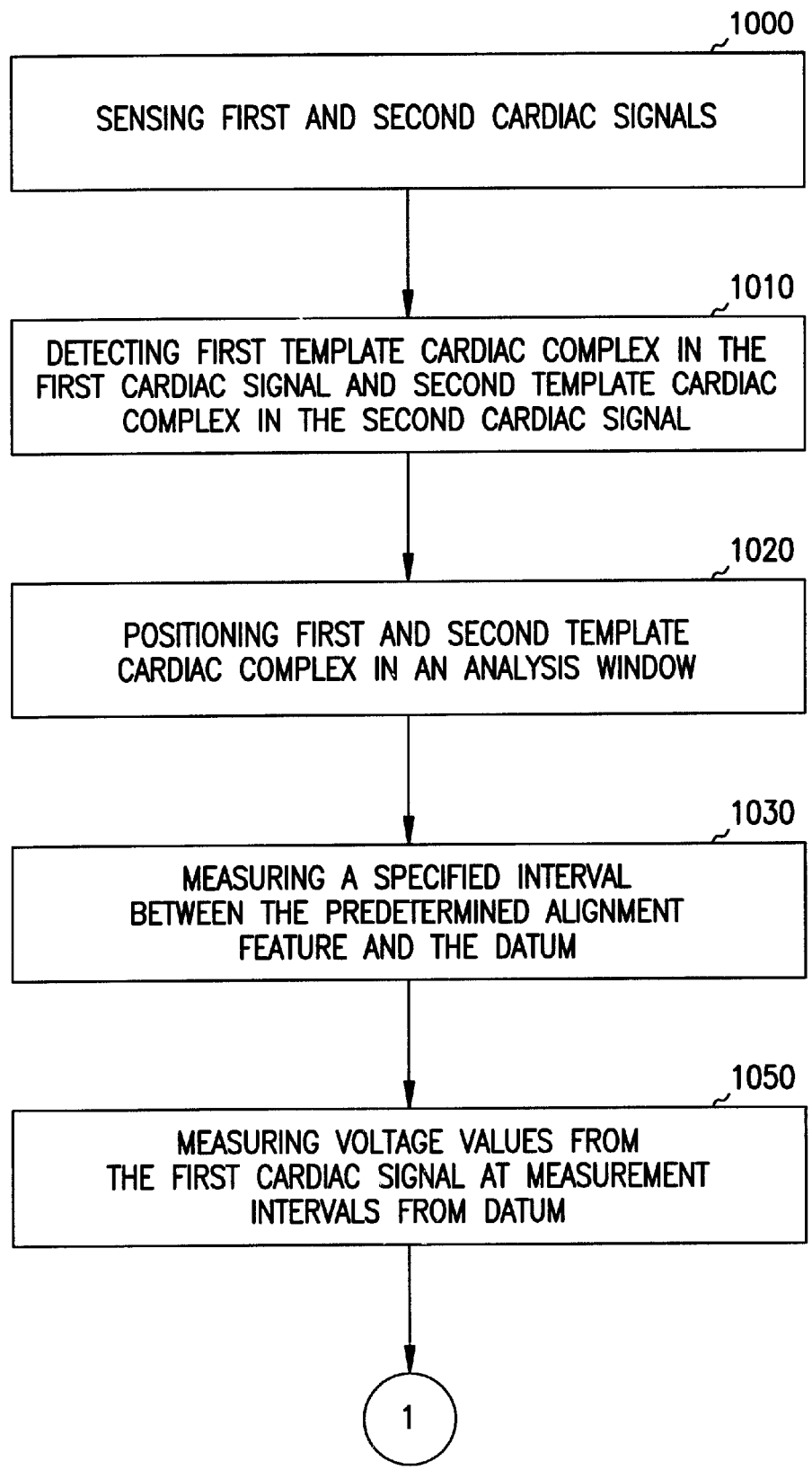
FIG. 10 is a flow diagram of one embodiment of the present subject matter.

Referring now to FIG. 10, there is shown an additional embodiment of the present subject matter. At 1000 a first cardiac signal and a second cardiac signal of a sensed cardiac complex are sensed. At 1010, first and second model cardiac complexes (e.g., NSR cardiac complexes or induced cardiac complexes) are detected in the first and second cardiac signals, respectively, as previously described. The first and second model cardiac complexes are then positioned in an analysis window at 1020. In one embodiment, the analysis window is a defined area around a portion of the first and second cardiac signals.

Figure 11:
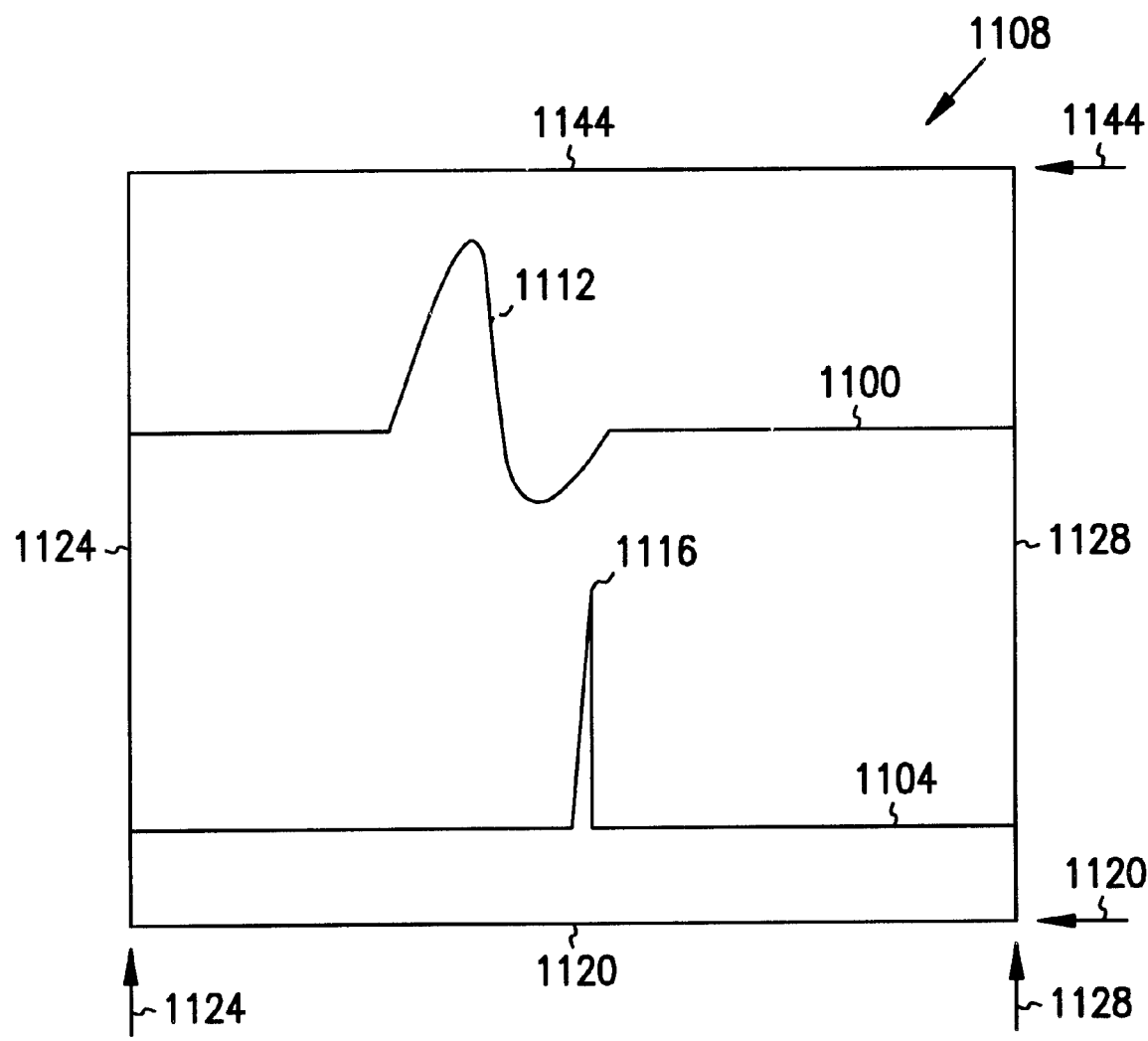
FIG. 11 shows a first cardiac signal and a second cardiac signal according to one embodiment of the present subject matter.

Referring now to FIG. 11, there is shown one embodiment of first and second cardiac signals, 1100 and 1104, positioned within an analysis window 1108. The analysis window 1108 is positioned around a first model cardiac complex 1112 and a second model cardiac complex 1116. In one embodiment, at least a portion of the analysis window 1108 is used as the datum for measuring the specified interval from the predetermined alignment feature on the second cardiac complex 1116. In one embodiment, the datum is selected from any position along a first horizontal axis 1120 of the analysis window 1108. For example, the datum could be selected from a vertical line 1124 positioned at the time the analysis window 1108 begins. Alternatively, the datum could be selected from a vertical line 1128 positioned at the time at which the analysis window 1108 ends.

Referring again to FIG. 10, once the analysis window has been positioned around the first and second model cardiac complex a predetermined alignment feature is selected, or identified, from the second model cardiac complex. Once the predetermined alignment feature of the second cardiac complex is identified, the specified interval is measured between the predetermined alignment feature and the datum at 1030. Once the datum is set relative the predetermined alignment feature the measurement interval is stored for use in classifying cardiac complexes. Voltage values of the first cardiac signal are then measured at the measurement intervals on the first model cardiac complex as previously described.

At 1150, voltage values of the first cardiac signal are measured from the first model cardiac complex relative the datum as previously described. The distance between each of the selected morphology features and the datum is then measured and the value of each of the distances creates a measurement interval. Each of the measurement intervals is then stored for subsequent use in locating a portion of the first cardiac signal sensed during a tachycardia episode. A voltage measurement of the first cardiac signal is then made at each of the measurement intervals and the TFV for the model cardiac complex is created and stored for subsequent use in analyzing cardiac complexes during a tachycardiac event.

Figure 12:
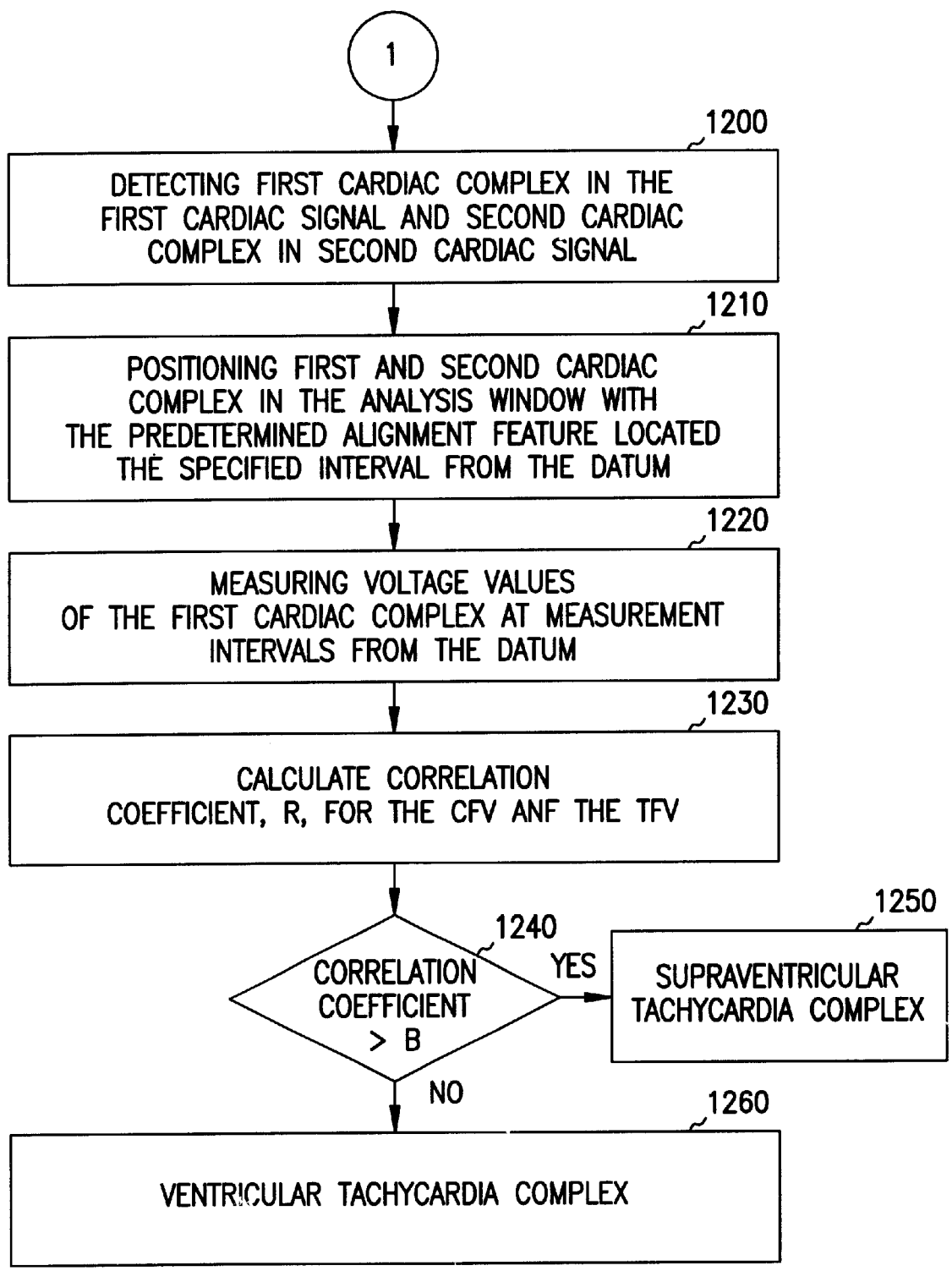
FIG. 12 is a flow diagram of one embodiment of the present subject matter.

In FIG. 12 there is shown one embodiment of classifying a cardiac complex according to the present subject matter. The encircled number 1 in FIG. 10 provides a link to the encircled number 1 in FIG. 12. At 1200, a first and second cardiac complex of a sensed cardiac complex is sensed in the first and second cardiac signals, respectively, during a tachycardia episode. At 1210, the first and second cardiac complex are positioned within an analysis window. The alignment feature is then located on the second cardiac complex. In one embodiment, the analysis window has the same horizontal axis dimension, or length, of the analysis window used for the first and second model cardiac complex in creating the TFV. The analysis window is then positioned around the first and second cardiac complex so the alignment feature is located at the specified interval from the datum.

Voltage values are then measured from the first cardiac signal at the measurement intervals at 1220. The voltage values for the first cardiac complex are then compared to the voltage values for the first model cardiac complex to determine whether the first cardiac complex is a VT complex or a SVT complex. In one embodiment, the comparison is accomplished by creating a CFV for the cardiac complex. The CFV and the TFV are then compared at 1230. In one embodiment, a correlation coefficient, r, is calculated for the CFV and the TFV. The correlation coefficient computed for the TFV and the CFV for the cardiac complex is then compared to the predetermined threshold, I, at 1240. When the correlation coefficient is greater than the predetermined threshold, the cardiac complex is classified as a SVT cardiac complex at 1250. When the correlation coefficient is less than or equal to the predetermined threshold, the cardiac complex is classified as a VT cardiac complex at 1260.

Figure 13:
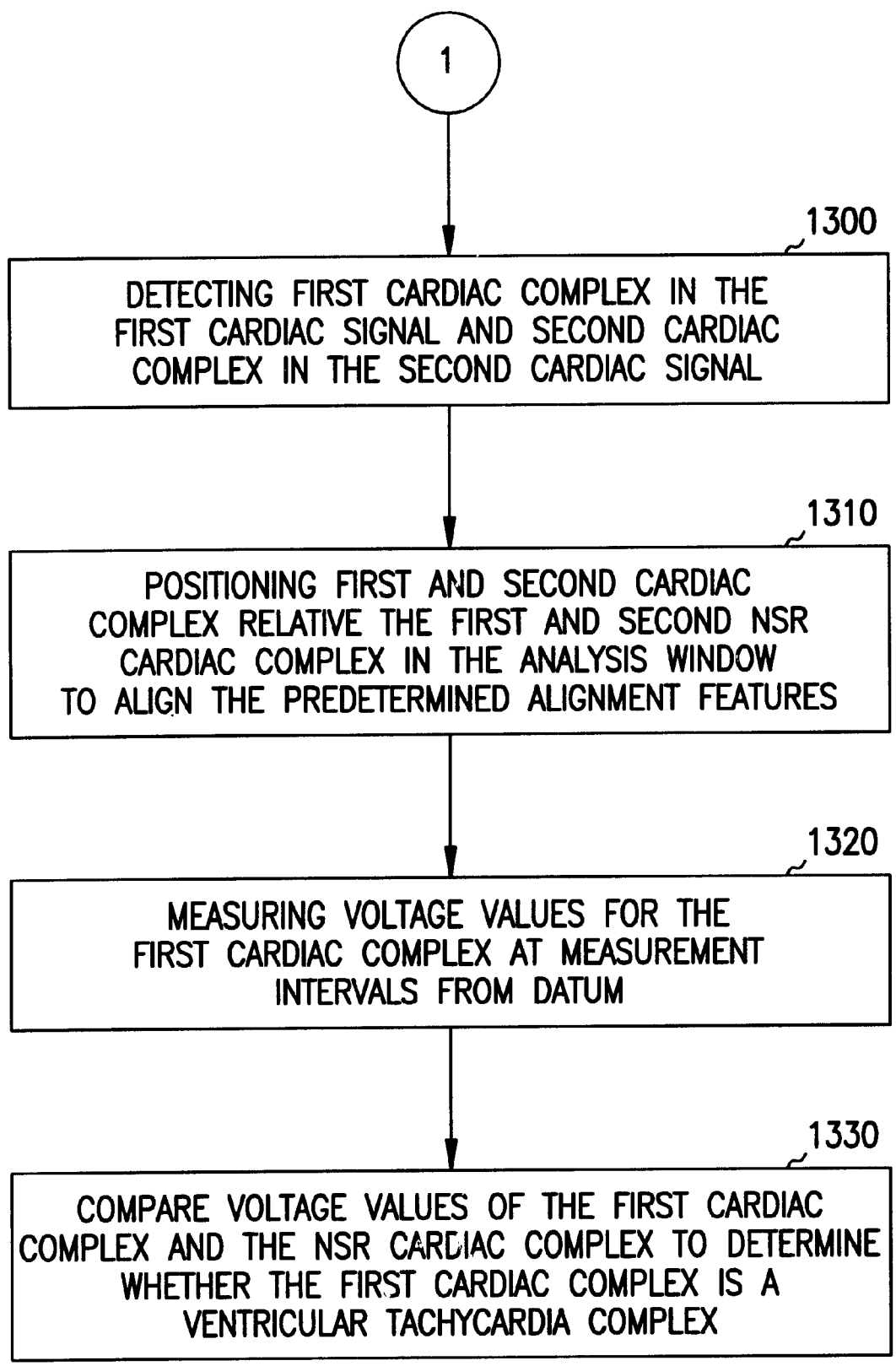
FIG. 13 is a flow diagram of one embodiment of the present subject matter.

Referring now to FIG. 13, there is shown an additional embodiment of the present subject matter. The encircled number 1 in FIG. 10 provides a link to the encircled number 1 in FIG. 13. At 1300, a first and second cardiac complex is sensed in the first and second cardiac signals, respectively, during a tachycardia episode. At 1310, the first and second cardiac complex are positioned relative the first and second model cardiac complexes within an analysis window. In one embodiment, the alignment feature of the second cardiac complex is located and then aligned with the alignment feature on the second model cardiac complex. In the present embodiment, the analysis window has the same horizontal axis dimension, or length, of the analysis window used for the first and second model cardiac complex in creating the TFV. The analysis window is then positioned around the first and second cardiac complex and the first and second model cardiac complex so the alignment feature on both the second model cardiac complex and the second cardiac complex are located at the measurement interval from the datum.

Figure 14:
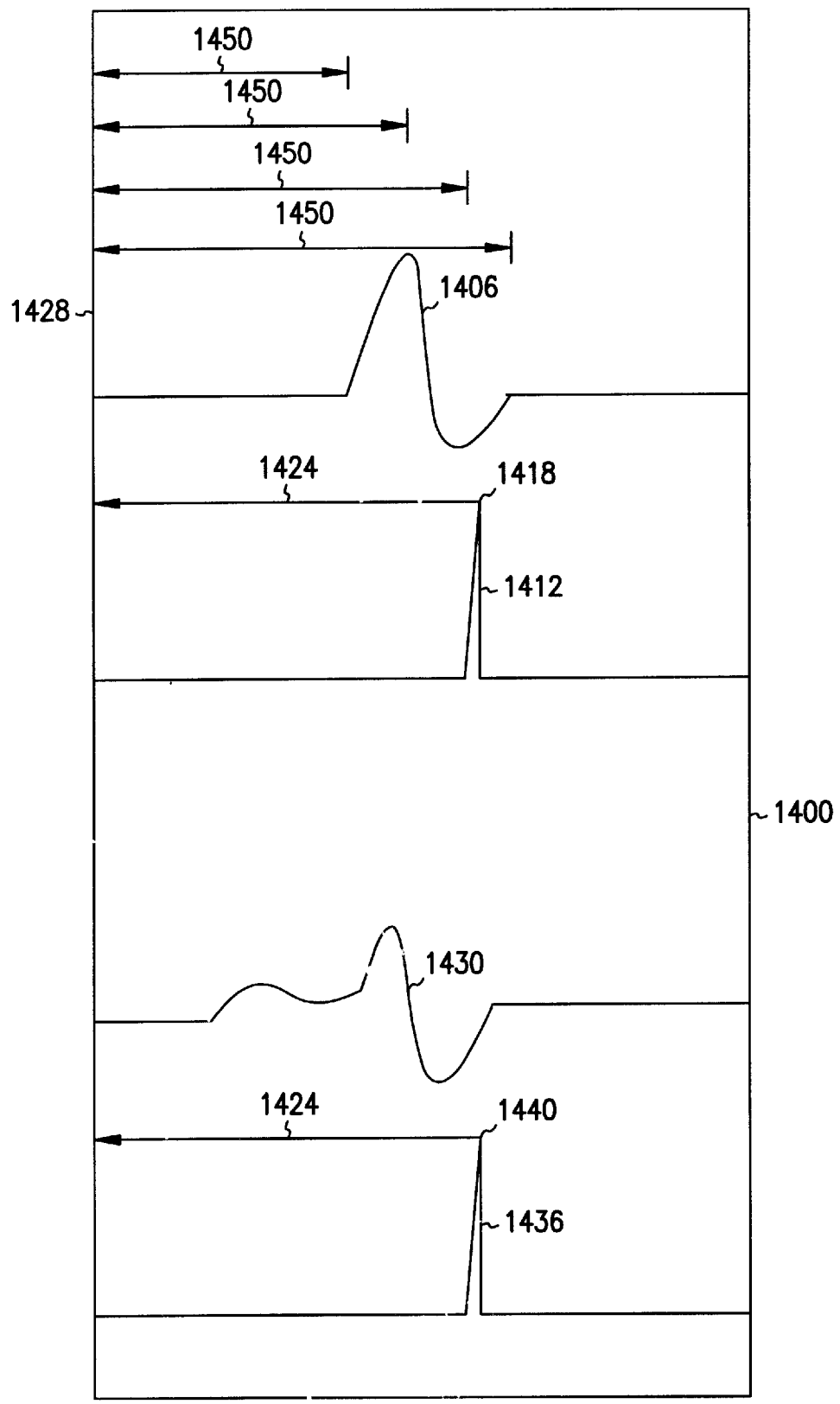
FIG. 14 shows first cardiac signals and second cardiac signals according to one embodiment of the present subject matter.

FIG. 14 shows one example of both the first and second cardiac complex and the first and second model cardiac complex aligned within an analysis window 1400. A first model cardiac complex 1406 and a second model cardiac complex 1412 are positioned within the analysis window 1400 with an alignment feature 1418 on the second model cardiac complex 1412 positioned at a specified interval 1424 from a datum 1428. A first cardiac complex 1430 and a second cardiac complex 1436 of a cardiac cycle sensed during a tachycardia episode are also positioned within the analysis window 1400. In one embodiment, a predetermined alignment feature 1440 on the second cardiac complex 1436 is aligned with the predetermined alignment feature 1418 on the second model cardiac complex 1412. Alternatively, the predetermined alignment feature 1440 on the second cardiac complex 1436 is positioned at the specified interval 1424 from the datum 1428.

Voltage values are then measured from the first cardiac signal at the measurement intervals 1450. The voltage value at each of the measurement intervals 1450 for the first cardiac complex are then compared to the voltage value in each of the measurement intervals 1450 for the first model cardiac complex to determine whether the first cardiac complex is a VT cardiac complex or a SVT cardiac complex. In one embodiment, the comparison is accomplished by creating a CFV for the cardiac complex. The CFV and the TFV are then compared at 1330. In one embodiment, a correlation coefficient, r, is calculated for the CFV and the TFV. The correlation coefficient computed for the TFV and the CFV for the cardiac complex is then compared to the predetermined threshold, A, at 1340. When the correlation coefficient is greater than the predetermined threshold, the cardiac complex is classified as a SVT cardiac complex at 1350. When the correlation coefficient is less than or equal to the predetermined threshold, the cardiac complex is classified as a VT cardiac complex at 1360.

In one embodiment, the present subject matter can be used in an implantable cardiac defibrillator (ICD) and/or an external medical device programmer. The present subject matter is compatible with ICD systems having one or more intracardiac leads having one or more electrodes which are able to sense a first and second cardiac signals. The present medical system can also be implemented in an external cardioverter/monitor system which includes surface electrodes and/or intracardiac leads having one or more electrodes. The present subject matter can also be implemented in an implantable atrial cardioverter-defibrillator, which may include numerous pacing modes known in the art. Furthermore, although the present system is described in conjunction with an implantable cardiac defibrillator having a microprocessor based architecture, it will be understood that the implantable cardiac defibrillator (or other implanted device) may be implemented in any logic based, custom integrated circuit architecture, if desired.

Figure 15:
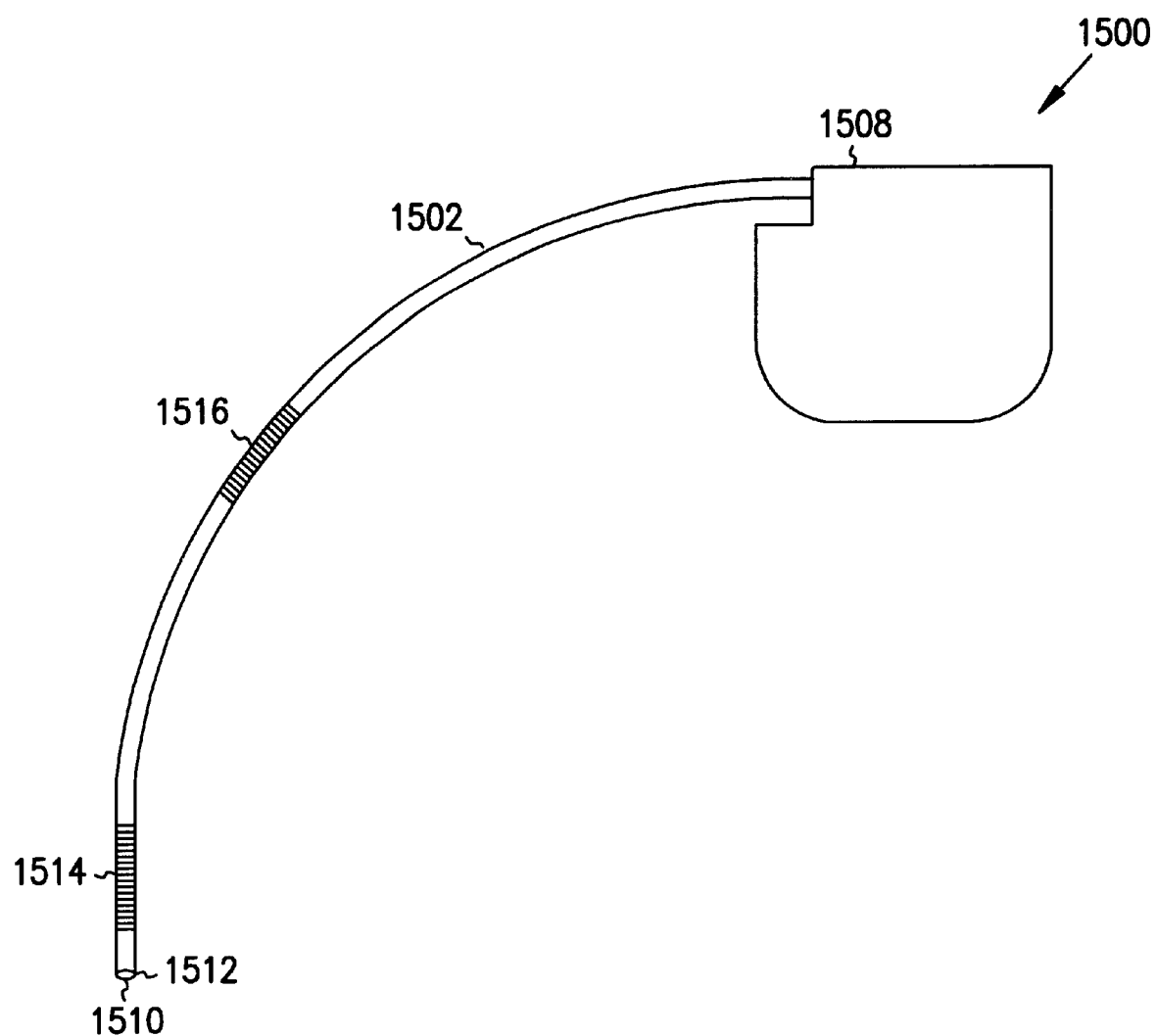
FIG. 15 is a schematic view of one embodiment of an implantable medical device with an endocardial lead and a medical device programmer.

Referring now to FIG. 15, there is shown one embodiment of a system, such as a medical device system, which includes at least one pacing electrode and at least a first defibrillation electrode and a second defibrillation electrode. In one embodiment, the system includes an implantable cardiac defibrillator 1500 electrically and physically coupled to at least one intracardiac catheter 1502. In the present embodiment the intracardiac catheter 1502 includes the at least one pacing electrode and the first and second defibrillation electrodes. Other catheter having either the first defibrillation electrode, the second defibrillation electrode or additional defibrillation electrodes could be included in the present system.

The intracardiac catheter 1502 shown in FIG. 15 is an endocardial lead adapted to be releasably coupled to the cardiac defibrillator 1500. The intracardiac catheter 1502 has an elongate body with a proximal end 1508 and a distal end 1510.

The intracardiac catheter 1502 includes a pacing electrode 1512 located at, or adjacent, the distal end 1510 of the intracardiac catheter 1502. Additional pacing electrodes can also be included on the intracardiac catheter 1502 to allow for bipolar sensing and pacing with the pacing electrode 1512. In addition, other pacing and sensing electrode configurations are also possible.

The intracardiac catheter 1502 further includes one or more defibrillation electrodes. The intracardiac catheter 1502 of FIG. 15 includes a first defibrillation electrode 1514 and a second defibrillation electrode 1516, where the first defibrillation electrode 1514 and the second defibrillation electrode 1516 are defibrillation coil electrodes. The first defibrillation electrode 1514 is spaced apart and proximal from the pacing electrode 1512, and the second defibrillation electrode 1516 is spaced apart and proximal from the first defibrillation electrode 1514. One example of intracardiac catheter 1502 is an Endotak catheter (CPI/Guidant, St. Paul, Minn.).

Figure 16:
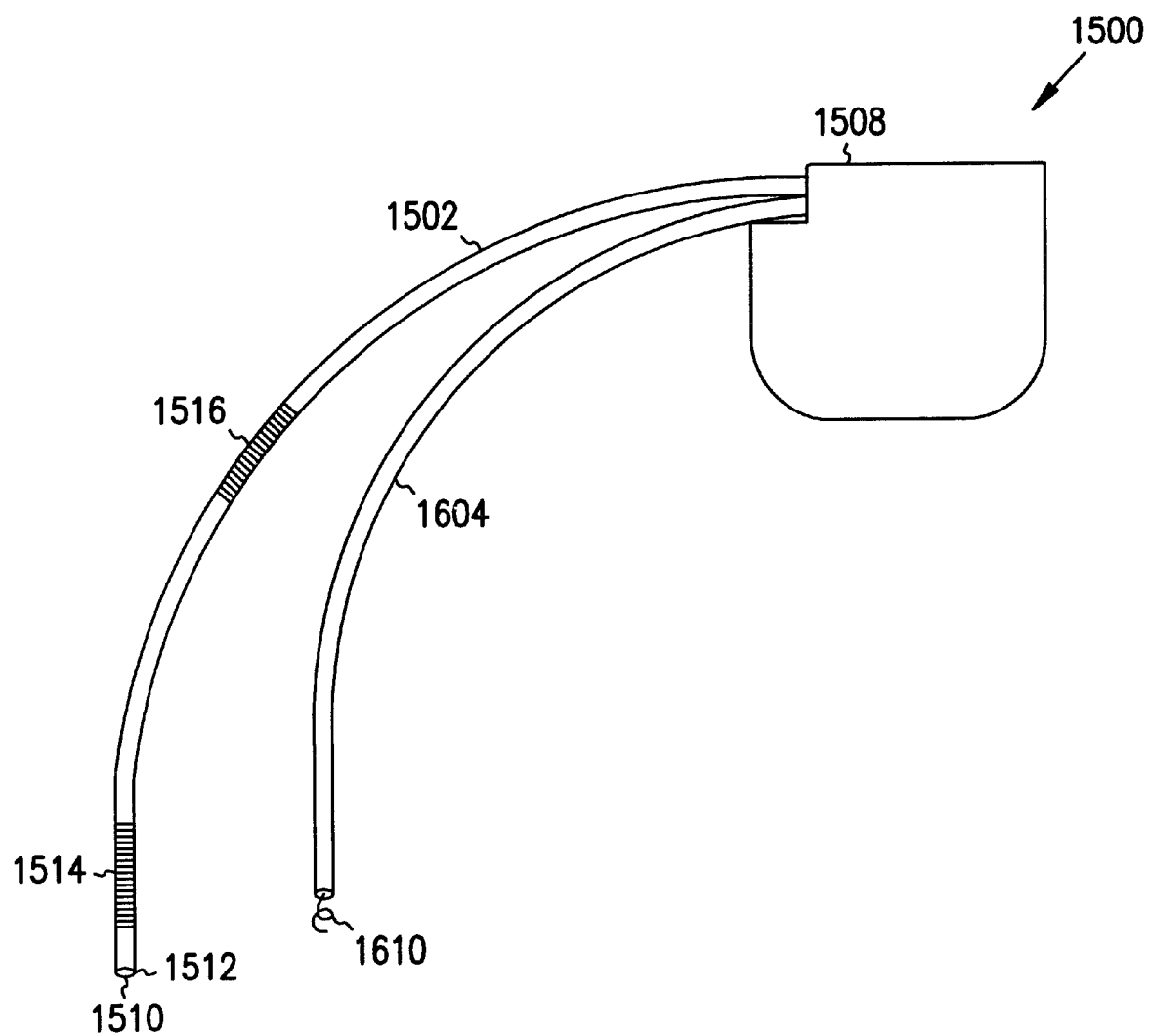
FIG. 16 is a schematic view of one embodiment of an implantable medical device with an endocardial lead and a medical device programmer.

Additional intracardiac catheters can be included with a medical device system. For example, FIG. 16 shows one embodiment of the implantable cardiac defibrillator 1500 having an intracardiac catheter 1502 as previously described and a second intracardiac catheter 1604. In one embodiment, the second intracardiac catheter 1604 includes a supraventricular pacing electrode 1610. In addition to the supraventricular pacing electrode 1610, the second intracardiac catheter 1604 can further include additional pacing/sensing electrodes and/or defibrillation electrodes as are known. Cardiac signals, such as an atrial cardiac signal, can be sensed from the pacing and defibrillation electrodes positioned on the second intracardiac catheter and delivered to the implantable cardiac defibrillator 1500 for analysis and electrical pulses can be delivered to the supraventricular pacing electrode 1610 according to the present subject matter.

Figure 17:
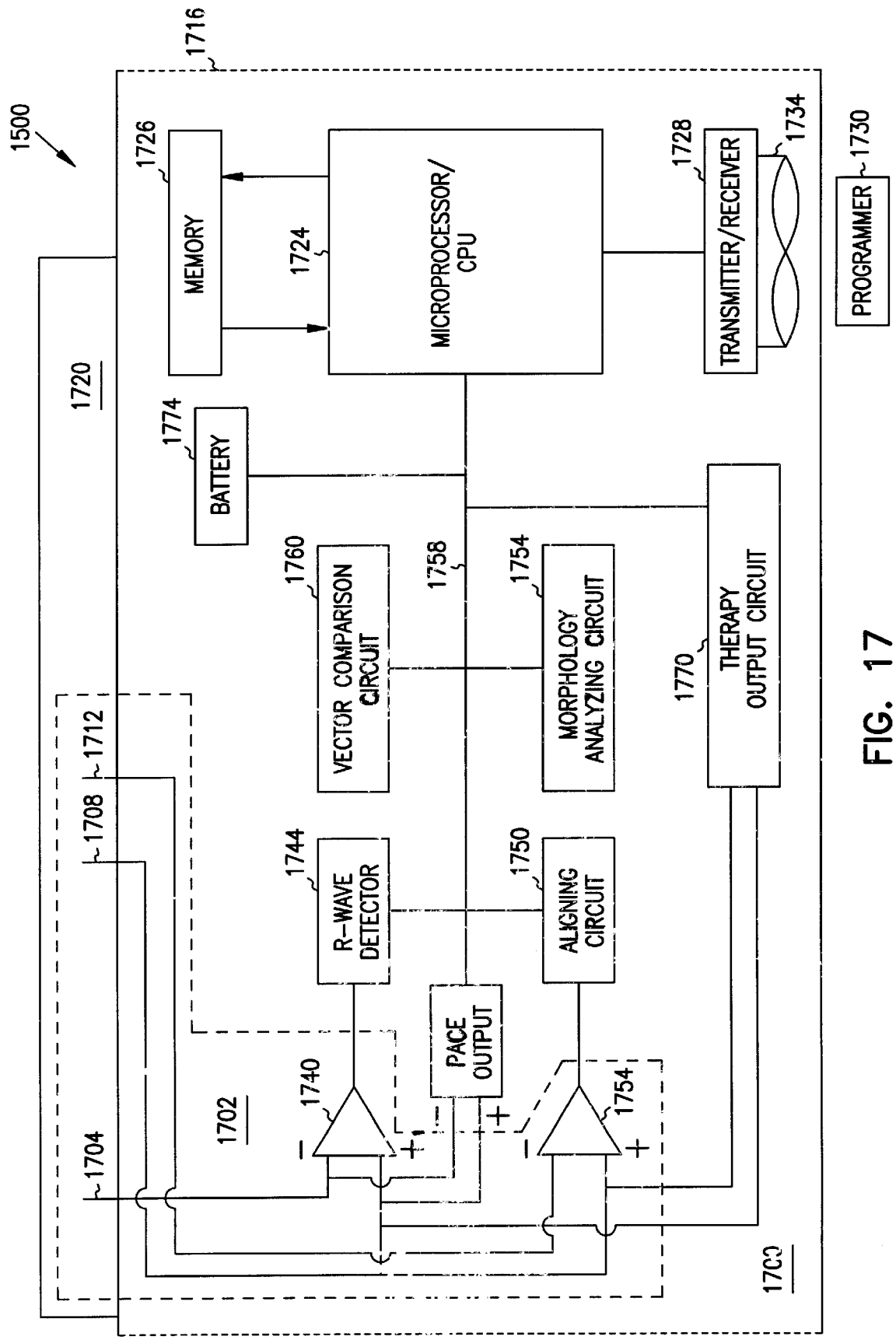
FIG. 17 is a block diagram of an implantable medical device according to one embodiment of the present system.

Referring now to FIG. 17, there is shown an embodiment of a block diagram of the system of FIG. 15 which includes the cardiac defibrillator 1500. The cardiac defibrillator 1500 includes control system circuitry 1700 which is coupled to a sensing system 1702. The sensing system 1702 includes terminals labeled with reference numbers 1704, 1708, and 1712 for connection to electrodes coupled to the surface of the intracardiac catheter 1502. The pacing electrode 1512 is electrically connected to terminal 1704 and to the control system circuitry 1700 through an electrically insulated conductor provided within the elongate body of the intracardiac catheter 1502. The first defibrillation electrode 1514 and the second defibrillation electrode 1516 are connected to terminals 1708 and 1712, respectively, and to the control system circuitry 1700 through electrically insulated conductors provided within the elongate body of the intracardiac catheter 1502.

In one embodiment, the control system circuitry 1700 is encased and hermetically sealed in a housing 1716 which is suitable for implanting in a human body. A connector block 1720 is additionally attached to the housing 1716 of the cardiac defibrillator 1500 to allow for the physical and the electrical attachment of the intracardiac catheter 1502 and the electrodes to the cardiac defibrillator 1500 and the encased control system circuitry 1700.

In one embodiment, the control system circuitry 1700 of the cardiac defibrillator 1500 is a programmable microprocessor-based system, with a microprocessor 1724 and a memory circuit 1726, which contains parameters for various pacing, defibrillation, and sensing modes and stores data indicative of cardiac signals received by the control system circuitry 1700. A transmitter circuit 1728 is additionally coupled to the control system circuitry 1700 and the memory circuit 1726 to allow the cardiac defibrillator 1500 to communicate with a medical device programmer 1730. In one embodiment, the transmitter circuit 1728 and the medical device programmer 1730 use a wire loop antenna 1734 and a radio frequency telemetric link, as is known in the art, to receive and transmit signals and data to and from the programmer unit 1730 and the control system circuitry 1700.

The second cardiac signal is a near-field signal sensed through the pacing electrode 1512. In the present embodiment, the pacing electrode 1512 and the first defibrillation electrode 1514 are used to sense the near-field cardiac signal or rate signal. In one embodiment, the pacing electrode 1512 and first defibrillation electrode 1514 are coupled to a sense amplifier 1740 within the sensing system 1702 to allow for the second cardiac signal as previously described to be sensed. In an alternative embodiment, the connections of the present control circuit is adapted to allow for the near-field cardiac signals to be sensed between the pacing electrode 1512 and the housing 1716.

In the present system, the first cardiac signal is a far-field signal. In one embodiment, the first cardiac signal is sensed between the first defibrillation electrode 1514 and the second defibrillation electrode 1516 which are coupled to the sense amplifier 1754. In an additional embodiment, the connections of the present control circuitry is adapted to allow for the first cardiac signal can also be sensed between the first defibrillation electrode 1514, the second defibrillation electrode 1516 and the housing 1530. The control system 1700 monitors the first cardiac signal for a first cardiac complex and the second cardiac signal for a second cardiac complex, where the first cardiac complex and the second cardiac complex represent a cardiac cycle.

The output of the sense amplifier 1740 is shown connected to an R-wave detector 1744 which is coupled to the control system 1700. In one embodiment, the R-wave detector 1744 determines the ventricular rate from the sensed cardiac complexes. The ventricular rate is then supplied to the microprocessor 1724. In one embodiment, the microprocessor 1724 analyzes the ventricular rate to detect when the ventricular rate exceeds a predetermined threshold. When the ventricular rate exceeds the predetermined threshold, the microprocessor 1724 declares a tachycardia episode. In one embodiment, the predetermined threshold is a programmable value set between 150 to 180 beats per minute.

When a tachycardia episode is declared, the R-wave detector circuit 1744 detects the second cardiac complex in the second cardiac signal and provides the second cardiac signal to an alignment circuit 1750 coupled to the control system 1700. In one embodiment, the alignment circuit 1750 analyzes the second cardiac complex to locate a predetermined alignment feature on the second cardiac complex and positions a datum at a specified interval from the alignment feature on the second cardiac complex.

The alignment circuit 1750 also receives the first cardiac signal and detects the first cardiac complex as the cardiac cycle is sensed. The alignment circuit 1750 receives the first cardiac complex and the second cardiac complex of the sensed cardiac cycle and analyzes the second cardiac complex to locate the predetermined alignment feature. In one embodiment, a location algorithm according to the present subject matter for identifying the alignment feature on the second cardiac complex is stored in the memory 1726 and executed in the alignment circuit 1750. The alignment circuit 1750 also positions the datum at the specified interval from the alignment feature on the second cardiac complex. In one embodiment, the specified interval of the datum is stored in memory 1726. In an alternative embodiment, the alignment circuit 1750 positions the analysis window around the first and second cardiac complex as previously described when an analysis window is used to isolate a cardiac complex in a first and second cardiac signal.

A morphology analyzing circuit 1754 is coupled to the alignment circuit 1750 of the control system 1700 via bus 1758. The morphology analyzing circuit 1754 measures the voltage value of the first cardiac signal at each of two or more measurement intervals from the datum. In one embodiment, the morphology analysis circuit 1754 retrieves the measurement intervals from the memory 1726. Once the first and second cardiac complex have been aligned relative to the datum, the morphology analyzing circuit 1754 measures the voltage of the first cardiac signal at each of the measurement intervals from the datum.

A vector comparison circuit 1760 is coupled to the control system 1700, including the morphology analyzing circuit 1754, via bus 1758. The vector comparison circuit 1760 receives the voltage values measured at the measurement intervals and creates the complex feature vector for each of the sensed cardiac complexes. The vector comparison circuit 1760 then compares the complex feature vector to the TFV. In one embodiment, the vector comparison circuit 1760 calculates the correlation coefficient between the TFV and the CFV of each of the sensed cardiac complexes. The vector comparison circuit 1760 then compares the correlation coefficient to the predetermined threshold, $\beta$. In one embodiment, the predetermined threshold is stored in the memory 1726. The vector comparison circuit 1760 classifies the cardiac complex as a SVT cardiac complex when the correlation coefficient is greater than the predetermined threshold and classifies the cardiac complex as a VT cardiac complex when the correlation coefficient is less than or equal to the predetermined threshold.

In one embodiment, the sensing system 1702 detects a plurality of the cardiac cycles in the first cardiac signal and the second cardiac signal. As the plurality of first cardiac complexes are sensed, the vector comparison circuit 1760 classifies a predetermined number of the first cardiac complexes. The microprocessor 1724 receives the classification of the cardiac complexes as they are classified by the vector comparison circuit 1760. In one embodiment, the predetermined number of the first cardiac complexes is a window of X cardiac complexes, where a new window is created as each subsequent cardiac complex is analyzed and classified. When a threshold number, Y, of X of the cardiac complexes are classified as VT complexes the control system 1700 declares a VT episode. Alternatively, when the Y of X counter fails to detect the threshold number of VT complexes in the X complex window, the ventricular arrhythmia is classified as a SVT episode. In an alternative embodiment, as the microprocessor 1724 receives the classification of the cardiac complexes a percentage of the classified cardiac complexes is calculated. The calculated percentage of VT complexes and SVT complexes sensed for the plurality of cardiac cycles during the tachycardia episode is compared to the threshold number, where the threshold number is a percentage value. So, a ventricular tachycardia episode is declared when the threshold number, or percentage, of the first cardiac complexes from the plurality of cardiac cycles are classified as ventricular tachycardia complexes. Alternatively, a supraventricular tachycardia episode is declared when the threshold number of the first cardiac complexes from the plurality of cardiac cycles are classified as supraventricular tachycardia complexes. In one embodiment, the threshold number is a programmable value in the range of 50 to 100 percent, where a value of approximately 70 percent is an acceptable value. The plurality of cardiac cycles sensed for classification and used in calculating the percentage of VT and SVT complexes is also a programmable number, where a value in the range of 8 to 50 classified complexes, where 10 is an acceptable value.

In one embodiment, once the ventricular episode has been classified, the microprocessor generates a signal which is delivered to a therapy output circuit 1770. In one embodiment, the therapy output circuit 1770 generates electrical energy (e.g., cardioversion and/or defibrillation electrical energy) which is delivered between the first and second defibrillation electrodes. Power for the cardiac defibrillator 1500 is supplied by an electrochemical battery 1774 that is housed within the cardiac defibrillator 1500.

Figure 18:
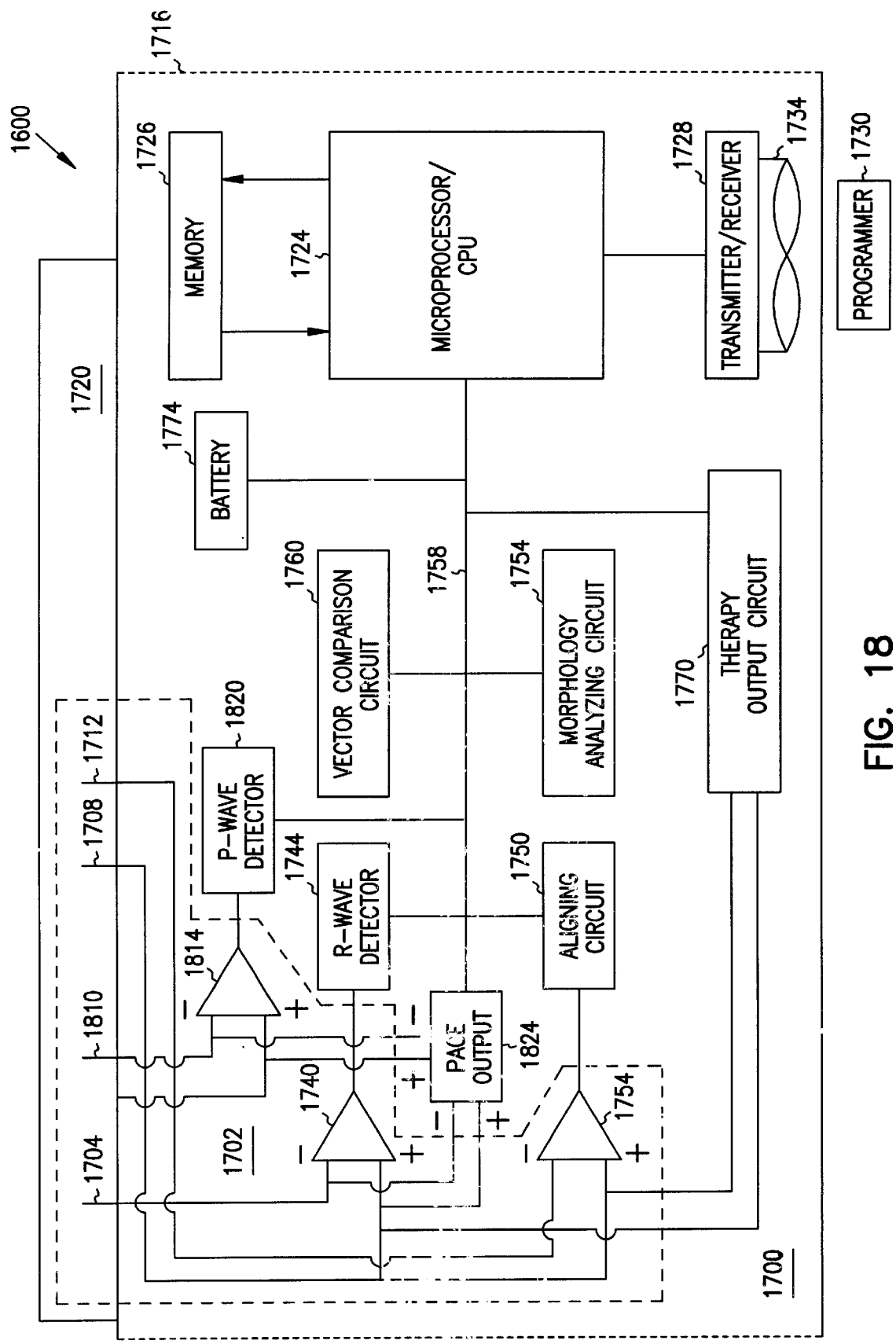
FIG. 18 is a block diagram of an implantable medical device according to one embodiment of the present system.

Referring now to FIG. 18, there is shown an embodiment of a block diagram of cardiac defibrillator 1500 shown in FIG. 16. The cardiac defibrillator 1500 of FIG. 18 includes all the components previously described in FIG. 17. In addition, the sensing system 1702 of the cardiac defibrillator 1500 further includes terminal 1810 for connection to the supraventricular pacing electrode 1610 which is coupled to the surface of the second intracardiac catheter 1604. In addition, the connector block 1720 further includes a second socket which is adapted to receive the second intracardiac catheter 1604.

The sensing system 1702 is used to detect an atrial cardiac signal with the supraventricular pacing electrode 1610. The control system 1700 monitors the atrial cardiac signal for atrial cardiac complexes and calculates an intrinsic atrial rate from the detected atrial cardiac complexes. In one embodiment, the sensing system 1702 includes an atrial signal sense amplifier 1814 which receives the atrial cardiac signal. The signal from the atrial signal sense amplifier 1814 is delivered to a P-wave detector circuit 1820 which detects the occurrence of atrial cardiac complexes (atrial contractions) from the atrial cardiac signal. The P-wave detector circuit 1820 is coupled to bus 1758 which allow for the microprocessor 1724 to calculate an intrinsic atrial rate, including an average intrinsic atrial rate, from the sensed atrial cardiac complexes.

The control system 1700 of FIG. 18 further includes a pace output circuit 1824. The pace output circuit 1824 is coupled to the terminal 1810 to allow for electrical pulses to be delivered to the supraventricular pacing electrode at the predetermined rate, which can be either at the intrinsic atrial rate or at a rate that is faster than the average intrinsic atrial rate as previously described. In one embodiment, the electrical pulses are delivered under the control of the control system 1700.

As previously described, the control system 1700 monitors the first cardiac signal for the first model cardiac complexes as electrical pulses are delivered to the supraventricular pacing electrode. The morphology analyzing circuit 1754 receives the detected first model cardiac complexes for the creation of a template. In one embodiment, the template is a classification algorithm which is used to classify subsequently detected cardiac complexes. Additionally, the morphology analyzing circuit creates a model cardiac complex from the first model cardiac complexes. Alternatively, the control system 1700 monitors the second cardiac signal for second model cardiac complexes as electrical pulses are delivered to the supraventricular pacing electrode. The R-wave detector circuit 1744 detects the second model cardiac complexes in the second cardiac signal and provides the second cardiac signal to the alignment circuit 1750. The alignment circuit 1750 analyzes each of the second model cardiac complexes to locate the predetermined alignment feature on each of the second model cardiac complexes. In addition, the alignment circuit 1750 positions the datum at the specified interval from the alignment feature on each of the second model cardiac complexes.

The morphology analyzing circuit 1754 then measures a voltage value of the first cardiac signal at each of two or more measurement intervals from the datum for each of the first model cardiac complexes. In one embodiment, once the morphology analyzing circuit 1754 has measured the voltage values of the cardiac signals the morphology analyzing circuit 1754 creates the template feature vector from the voltage value of the first cardiac signal at each of two or more measurement intervals from the datum for each of the first model cardiac complexes. In an alternative embodiment, the model cardiac complexes detected in the first and/or second cardiac complexes are downloaded to the programmer 1730. Once downloaded, the programmer 1730 is used to create the template from the model cardiac complexes. The template is then transmitted back to the control system 1700 where it is stored in memory 1726 for use in analyzing and classifying cardiac complexes sensed during a tachycardia episode.

I claim:

1. A method, comprising:

sensing a first cardiac signal and a second cardiac signal, wherein the first cardiac signal has a voltage;

detecting a first cardiac complex of a cardiac cycle in the first cardiac signal;

detecting a second cardiac complex of the cardiac cycle in the second cardiac signal, wherein the second cardiac complex includes a predetermined alignment feature;

defining a datum at a specified interval from the predetermined alignment feature of the second cardiac complex;

selecting two or more morphological features along the first cardiac complex;

obtaining two or more predefined measurement intervals from the datum, the two or more predefined measurement intervals being measured between the datum and the respective two or more morphological features; and measuring a voltage value of the first cardiac signal for the first cardiac complex at each of the two or more predefined measurement intervals from the datum.

2. The method of claim 1, including:

detecting a first model cardiac complex in the first cardiac signal;

detecting a second model cardiac complex in the second cardiac signal;

locating a predetermined alignment feature relative the second model cardiac complex;

measuring the specified interval between the predetermined alignment feature and the datum;

storing the specified interval;

measuring a voltage value of the first cardiac signal for the first model cardiac complex at each of the two or more measurement intervals from the datum; and storing the voltage values of the first cardiac signal for the first model cardiac complex at each of the two or more measurement intervals from the datum.

3. The method of claim 2, wherein detecting the first model cardiac complex includes detecting a first normal sinus rhythm (NSR) cardiac complex of a NSR cardiac cycle in the first cardiac signal;

wherein detecting the second model cardiac complex includes detecting a second NSR cardiac complex of the NSR cardiac cycle in the second cardiac signal; and locating the predetermined alignment feature includes identifying the predetermined alignment feature in the second NSR cardiac complex.

4. The method of claim 3, including positioning the first NSR cardiac complex and the second NSR cardiac complex in an analysis window, wherein the analysis window includes the datum from which voltage values of the first cardiac signal are measured; and positioning the first cardiac complex and the second cardiac complex relative the first NSR cardiac complex and the second NSR cardiac complex in the analysis window to align the predetermined alignment feature of the second cardiac complex and the second NSR cardiac complex.

5. The method of claim 2, wherein detecting the first model cardiac complex in the first cardiac signal includes:

delivering electrical pulses to a supraventricular location;

detecting the first cardiac signal as the electrical pulses are delivered to the supraventricular location.

6. The method of claim 5, including detecting an atrial cardiac signal;

detecting atrial cardiac complexes in the atrial cardiac signal;

calculating an average intrinsic atrial rate from the detected atrial cardiac complexes; and wherein delivering electrical pulses to the supraventricular location includes delivering electrical pulses to the supraventricular location at a predetermined rate which is faster than the average intrinsic atrial rate.

7. The method of claim 2, including:

detecting a tachycardia episode;

sensing the first cardiac complex of the first cardiac signal and the second cardiac complex of the second cardiac signal during the tachycardia episode;

comparing the stored voltage values of the first model cardiac complex to the voltage values of the first cardiac complex measured during the tachycardia episode; and determining whether the first cardiac complex is a ventricular tachycardia complex based on the comparison.

8. The method of claim 7, including calculating a correlation coefficient from the stored voltage values of the first model cardiac signal and the measured voltage values of the first cardiac signal;

classifying the first cardiac complex as a VT complex when the correlation coefficient is less than or equal to a predetermined threshold; and classifying the first cardiac complex as an SVT complex when the correlation coefficient is greater than the predetermined threshold.

9. The method of claim 8, including detecting, over a plurality of cardiac cycles, first cardiac complexes in the first cardiac signal and second cardiac complexes in the second cardiac signal;

classifying a predetermined number of the first cardiac complexes;

declaring a ventricular tachycardia episode when a threshold number of the predetermined number of the first cardiac complexes are classified as ventricular tachycardia complexes; and declaring a supraventricular tachycardia episode when the threshold number of the predetermined number of the first cardiac complexes are classified as supraventricular tachycardia complexes.

10. The method of claim 8, including detecting, over a plurality of cardiac cycles, first cardiac complexes in the first cardiac signal and second cardiac complexes in the second cardiac signal;

declaring a ventricular tachycardia episode when a threshold percentage of the first cardiac complexes from the plurality of cardiac cycles are classified as ventricular tachycardia complexes; and declaring a supraventricular tachycardia episode when the threshold percentage of the first cardiac complexes from the plurality of cardiac cycles are classified as supraventricular tachycardia complexes.

11. The method of claim 7, including multiplying the specified interval by a scaling percentage to give a revised specified interval;

defining the datum at the revised specified interval from the predetermined alignment feature of the second cardiac complex;

multiplying each of the two or more measurement intervals by the scaling percentage to give revised measurement intervals; and measuring the voltage value of the first cardiac signal for the first cardiac complex at each of two or more revised measurement intervals from the datum.

12. The method of claim 1, including positioning the first cardiac complex and the second cardiac complex in an analysis window, wherein the analysis window includes the datum from which voltage values of the first cardiac signal are measured.

13. The method of claim 1, wherein the predetermined alignment feature is a repeatably identifiable portion of the second cardiac complex.

14. The method of claim 13, wherein the predetermined alignment feature is a point of at least one of a maximum deflection and a maximum slew.

15. The method of claim 1, wherein each of the two or more the morphological features includes a repeatably identifiable portion of the first cardiac complex.

16. The method of claim 15, wherein each of the two or more of the morphological features includes at least one of a maximum deflection point, a minimum deflection point, a beginning of the first cardiac complex, and an ending of the first cardiac complex.

* * * * *